US006355789B1

(12) United States Patent
Alizon et al.

(10) Patent No.: US 6,355,789 B1
(45) Date of Patent: Mar. 12, 2002

(54) CLONED DNA SEQUENCES RELATED TO THE ENTIRE GENOMIC RNA OF HUMAN IMMUNODEFICIENCY VIRUS II (HIV-2), POLYPEPTIDES ENCODED BY THESE DNA SEQUENCES AND USE OF THESE DNA CLONES AND POLYPEPTIDES IN DIAGNOSTIC KITS

(75) Inventors: Marc Alizon, Paris; Luc Montagnier, Le Plessis Robinson; Denise Geutard, Paris, all of (FR); Francois Clavel, Rockville, MD (US); Pierre Sonigo; Mireille Guyader, both of Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 08/468,424

(22) Filed: Jun. 6, 1995

Related U.S. Application Data

(63) Continuation of application No. 08/214,221, filed on Mar. 17, 1994, now Pat. No. 5,580,739, which is a division of application No. 07/810,908, filed on Dec. 20, 1991, which is a division of application No. 07/752,368, filed on Sep. 3, 1991, now abandoned, which is a division of application No. 07/013,477, filed on Feb. 11, 1987, now Pat. No. 5,079,342, which is a continuation-in-part of application No. 07/003,764, filed on Jan. 16, 1987, now Pat. No. 5,051,496, which is a continuation-in-part of application No. 06/933,184, filed on Nov. 21, 1986, now abandoned, which is a continuation-in-part of application No. 06/916,080, filed on Oct. 6, 1986, now abandoned, which is a continuation-in-part of application No. 06/835,228, filed on Mar. 3, 1986, now Pat. No. 4,839,288.

(30) Foreign Application Priority Data

| | | |
|---|---|---|
| Jan. 22, 1986 | (FR) | 86 00911 |
| Feb. 6, 1986 | (FR) | 86 01635 |
| Feb. 13, 1986 | (FR) | 86 01985 |
| Mar. 18, 1986 | (FR) | 86 03881 |
| Mar. 24, 1986 | (FR) | 86 04215 |

(51) Int. Cl.[7] ............ C07H 21/04

(52) U.S. Cl. ............ 536/23.72; 536/23.1; 424/188.1; 424/208.1

(58) Field of Search ............ 435/91.32, 91.51, 435/172.3; 424/208.1; 536/23.77

(56) References Cited

U.S. PATENT DOCUMENTS

| | | | | |
|---|---|---|---|---|
| 4,629,783 A | 12/1986 | Cosand | 424/188.1 |
| 4,839,288 A | 6/1989 | Montagnier et al. | 435/235 |
| 5,079,342 A | 1/1992 | Alizon et al. | 530/324 |
| 5,670,309 A | 9/1997 | Norrby et al. | 435/5 |

FOREIGN PATENT DOCUMENTS

| | | |
|---|---|---|
| EP | 0 316 695 B1 | 3/1993 |
| WO | WO 85/04897 | 11/1985 |

OTHER PUBLICATIONS

Gao, F., et al., 1994, "Genetic diversity of human immunodeficiency virus type 2: Evidence for distinct sequence subtypes with differences in virus biology.", J. Virol. 68(11):7433–7447.*

Goodenow, M., et al., 1989, "HIV–1 isolates are rapidly evolving quasispecies: Evidence for viral mixtures and preferred nucleotide substitutions.", J. Acquir. Immun. Defic. Syndr. 2:344–352.*

Holland, J.J., et al., 1992, "RNA virus populations as quasispecies", Curr. Topics Microbiol. Immunol. 176:1–20.*

Los Alamos Database, 1990, in Human Retroviruses and AIDS, Myers et al., eds., Los Alamos National Laboratory, New Mexico, pp. IA1–IA3.*

Tedder et al., 1988, The Lancet 2:927–931.*

Hunt et al., 1990, AIDS Res. Human Retro. 6:883–898.*

Strongin, W., 1992, "Sensitivity, specificity, and predictive value of diagnostic tests: definitions and clinical applications", in Laboratory Diagnosis of Viral Infections, Lennette ed., Marcel Dekker, Inc. New York, pp. 211–219.*

Clavel et al., "Isolation of a New Human Retrovirus from West African Patients with AIDS", *Science,* 233, pp. 343–346 (1986).

Allan et al., "Major Glycoprotein Antigens That Induce Antibodies in AIDS Patients Are Encoded by HTLV–III," *Science,* 228, pp. 1091–1094 (1985).

(List continued on next page.)

*Primary Examiner*—Laurie Scheiner
*Assistant Examiner*—Jeffrey S. Parkin
(74) *Attorney, Agent, or Firm*—Finnegan, Henderson, Farabow, Garrett, & Dunner, LLP

(57) ABSTRACT

The present invention is directed toward nucleic acids containing the full-length human immunodeficiency virus type 2 ROD (HIV-$2_{ROD}$) pol gene. HIV-2, which was originally designated lymphadenopathy-associated virus type II (LAV-II), was isolated from AIDS patients in West Africa. The virus is genotypically and phenotypically distinct from HIV-1 and bears a closer genetic relationship to the simian immunodeficiency virus (SIV). The present invention describes the preparation of HIV-$2_{ROD}$ proviral molecular clones from a genomic lambda phage library of $CD4^+$-infected cells. The complete nucleotide sequence of the full-length genome was determined and the putative gag, pol, env, vif (Q), vpr (R), vpx (X), nef (F), tat, and rev (art) genes identified. The claimed invention is directed toward nucleic acids containing the full-length HIV-$2_{ROD}$ pol gene (nt 1829-4936). These nucleic acids should prove useful as diagnostic reagents for the detection of HIV-2 and facilitate expression of the pol gene product.

1 Claim, 5 Drawing Sheets

OTHER PUBLICATIONS

Chang et al., "Detection of Antibodies to Human T–Cell Lymphotropic Virus–III (HTLV–III) with an Immunoassay Employing a Recombinant *Escherichia coli*–Derived Viral Antigenic Peptide," *Bio/Technology*, 3, pp. 905–909 (1985).

Kanki et al., "Isolation of T–lymphotropic Retrovirus Related to HTLV–III/LAV from Wild–Caught African Green Monkeys," *Science*, 230, pp. 951–954 (1985).

Kanki et al., "Serologic Identification and Characterization of a Macaque T–lymphotropic Retrovirus Closely Related to HTLV–III," *Science*, 228, pp. 1199–1201 (1985).

Clavel et al., "LAV Type II: A Second Retrovirus Associated With AIDS In West Africa," *C.R. Acad. Sc. Paris*, Serie III, 302, pp. 485–488 (1986).

Klatzmann et al., "T–lymphocyte T4 Molecule Behaves As The Receptor For Human Retrovirus LAV," *Nature*, 312, pp. 767–768 (1984).

Daniel et al., "Isolation of T–Cell Tropic HTLV–III–like Retrovirus from Macaques," *Science*, 228, pp. 1201–1204 (1985).

Barin et al., "Serological Evidence For Virus Related to Simian T–lymphotropic Retrovirus III in Residents of West Africa," *The Lancet*, pp. 1387–1389 (Dec. 21/28, 1985).

Sandstrom et al., "Antiviral Therapy In AIDS Clinical Pharmacological Properties and Therapeutic Experience to Date," *Drugs*, 34, pp. 372–390 (1987).

Mitsuya et al., "Protection of T Cells Against Infectivity and Cytopathic Effect of HTLV–III In Vitro," Retroviruses in Human Lymphoma/Leukemia, M. Miwa et al., eds., pp. 277–288 (Japan Science Press, Tokyo, 1985).

Gallo et al., "HIV/HTLV gene nomenclature", Nature 333:564 (1988).

Laurence, J., "Summary of HIV–1 and HIV–2 nomenclature", AIDS Res. Hum. Retro. 4:vii–viii (1988).

(a) Clavel et al., "Isolation of a new human retrovirus from West African patients with AIDS", Science 233:343–347 (1986).

(b) Clavel et al., "Molecular cloning and polymorphism of the human immunodeficiency virus type 2", Nature 324:691–695 (1986).

\* cited by examiner

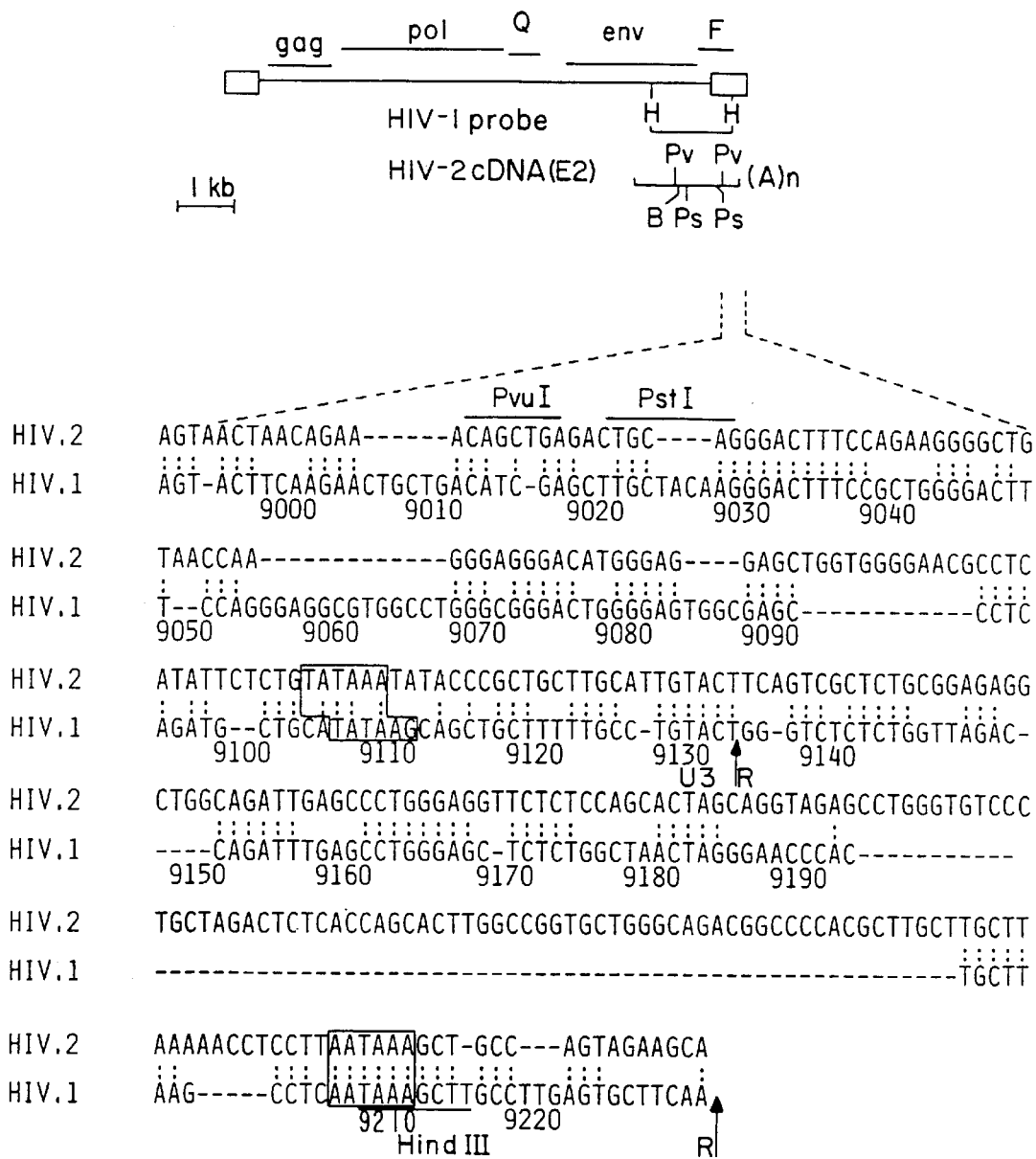

CLONED DNA SEQUENCES RELATED TO THE ENTIRE GENOMIC RNA OF HUMAN IMMUNODEFICIENCY VIRUS II (HIV-2), POLYPEPTIDES ENCODED BY THESE DNA SEQUENCES AND USE OF THESE DNA CLONES AND POLYPEPTIDES IN DIAGNOSTIC KITS

This is a division of application Ser. No. 08/214,221, filed Mar. 17, 1994, now U.S. Pat. No. 5,580,739, which is a divisional of application Ser. No. 07/810,908, filed Dec. 20, 1991, which is a divisional of application Ser. No. 07/752,368, filed Sept. 3, 1991 abandoned, which is a divisional of application Ser. No. 07/013,477, filed Feb. 11, 1987, (now U.S. Patent No. 5,079,342), which is a CIP of application Ser. No. 07/003,764, filed Jan. 16, 1987, (now U.S. Pat. No. 5,051,496), which is a CIP of application Ser. No. 06/933,184, filed Nov. 21, 1986 abandoned, which is a CIP of application Ser. No. 06/916,080, filed Oct. 6, 1986 abandoned, which is a CIP of application Ser. No. 06/835,228, filed Mar. 3, 1986 now U.S. Pat. No. 4,839,288.

BACKGROUND OF THE INVENTION

The invention relates to cloned DNA sequences analogous to the genomic RNA of a virus known as Lymphadenopathy-Associated Virus II ("LAV-II"), a process for the preparation of these cloned DNA sequences, and their use as probes in diagnostic kits. In one embodiment, the invention relates to a cloned DNA sequence analogous to the entire genomic RNA of HIV-2 and its use as a probe. The invention also relates to polypeptides with amino acid sequences encoded by these cloned DNA sequences and the use of these polypeptides in diagnostic kits.

According to recently adopted nomenclature, as reported in Nature, May 1986, a substantially-identical group of retroviruses which has been identified as one causative agent of AIDS are now referred to as Human Immunodeficiency Viruses I (HIV-1). This previously-described group of retroviruses includes Lymphadenopathy-Associated Virus I (LAV-I), Human T-cell Lymphotropic Virus-III (HTLV-III), and AIDS-Related Virus (ARV).

Lymphadenopathy-Associated Virus II has been described in U.S. application Ser. No. 835,228, which was filed Mar. 3, 1986, and is specifically incorporated herein by reference. Because LAV-II is a second, distinct causative agent of AIDS, LAV-II properly is classifiable as a Human Immunodeficiency Virus II (HIV-2). Therefore, "LAV-II" as used hereinafter describes a particular genus of HIV-2 isolates.

While HIV-2 is related to HIV-1 by its morphology, its tropism and its in vitro cytopathic effect on CD4 (T4) positive cell lines and lymphocytes, HIV-2 differs from previously described human retroviruses known to be responsible for AIDS. Moreover, the proteins of HIV-1 and 2 have different sizes and their serological cross-reactivity is restricted mostly to the major core protein, as the envelope glycoproteins of HIV-2 are not immune precipitated by HIV-1-positive sera except in some cases where very faint cross-reactivity can be detected. Since a significant proportion of the HIV infected patients lack antibodies to the major core protein of their infecting virus, it is important to include antigens to both HIV-1 and HIV-2 in an effective serum test for the diagnosis of the infection by these viruses.

HIV-2 was first discovered in the course of serological research on patients native to Guinea-Bissau who exhibited clinical and immunological symptoms of AIDS and from whom sero-negative or weakly sero-positive reactions to tests using an HIV-1 lysate were obtained. Further clinical studies on these patients isolated viruses which were subsequently named "LAV-II."

One LAV-II isolate, subsequently referred to as LAV-II MIR, was deposited at the Collection Nationale des Cultures de Micro-Organismes (CNCM) at the Institute Pasteur in Paris, France on Dec. 19, 1985 under Accession No. I-502 and has also been deposited at the British ECA CC under No. 87.001.001 on Jan. 9, 1987. A second LAV-II isolate was deposited at CNCM on Feb. 21, 1986 under Accession No. I-532 and has also been deposited at the British ECA CC under No. 87.001.002 on Jan. 9, 1987. This second isolate has been subsequently referred to as LAV-II ROD. Other isolates deposited at the CNCM on Dec. 19, 1986 are HIV-2 IRMO (No. I-642) and HIV-2 EHO (No. 1-643). Several additional isolates have been obtained from West African patients, some of whom have AIDS, others with AIDS-related conditions and others with no AIDS symptoms. All of these viruses have been isolated on normal human lymphocyte cultures and some of them were thereafter propagated on lymphoid tumor cell lines such as CEM and MOLT.

Due to the sero-negative or weak sero-positive results obtained when using kits designed to identify HIV-1 infections in the diagnosis of these new patients with HIV-2 disease, it has been necessary to devise a new diagnostic kit capable of detecting HIV-2 infection, either by itself or in combination with an HIV-1 infection. The present inventors have, through the development of cloned DNA sequences analogous to at least a portion of the genomic RNA of LAV-II ROD viruses, created the materials necessary for the development of such kits.

SUMMARY OF THE INVENTION

As noted previously, the present invention relates to the cloned nucleotide sequences homologous or identical to at least a portion of the genomic RNA of HIV-2 viruses and to polypeptides encoded by the same. The present invention also relates to kits capable of diagnosing an HIV-2 infection.

Thus, a main object of the present invention is to provide a kit capable of diagnosing an infection caused by the HIV-2 virus. This kit may operate by detecting at least a portion of the RNA genome of the HIV-2 virus or the provirus present in the infected cells through hybridization with a DNA probe or it may operate through the immunodiagnostic detection of polypeptides unique to the HIV-2 virus.

Additional objects and advantages of the present invention will be set forth in part in the description which follows, or may be learned from practice of the invention. The objects and advantages may be realized and attained by means of the instrumentalities and combinations particularly pointed out in the appended claims.

To achieve these objects and in accordance with the purposes of the present invention, cloned DNA sequences related to the entire genomic RNA of the LAV-II virus are set forth. These sequences are analogous specifically to the entire genome of the LAV-II ROD strain.

To further achieve the objects and in accordance with the purposes of the present invention, a kit capable of diagnosing an HIV-2 infection is described. This kit, in one embodiment, contains the cloned DNA sequences of this invention which are capable of hybridizing to viral RNA or analogous DNA sequences to indicate the presence of an HIV-2 infection. Different diagnostic techniques can be used which include, but are not limited to: (1) Southern blot procedures to identify viral DNA which may or may not be digested with restriction enzymes; (2) Northern blot techniques to identify viral RNA extracted from cells; and (3) dot blot techniques, i.e., direct filtration of the sample through an ad hoc membrane such as nitrocellulose or nylon without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by ultra-centrifugation as accomplished in the "CYTODOT" procedure as described in a booklet published by Schleicher and Schull.

In an alternate embodiment, the kit contains the polypeptides created using these cloned DNA sequences. These polypeptides are capable of reacting with antibodies to the HIV-2 virus present in sera of infected individuals, thus yielding an immunodiagnostic complex.

To further achieve the objects of the invention, a vaccinating agent is provided which comprises at least one peptide selected from the polypeptide expression products of the viral DNA in admixture with suitable carriers, adjuvents stabilizers.

It is understood that both the foregoing general description and the following detailed description are exemplary and explanatory only and are not restrictive of the invention as claimed. The accompanying drawings, which are incorporated in and constitute a part of the specification, illustrate one embodiment of the invention and, together with the description, serve to explain the principles of the invention.

BRIEF DESCRIPTION OF THE DRAWINGS

FIG. 1 generally depicts the nucleotide sequence of a cloned complementary DNA (cDNA) to the genomic RNA of HIV-2. FIG. 1A depicts the genetic organization of HIV-1, position of the HIV-1 HindIII fragment used as a probe to screen the cDNA library, and restriction map of the HIV-2 cONA clone, E2. FIG. 1B depicts the nucleotide sequence of the 3' end of HIV-2. The corresponding region of the HIV-1 LTR was aligned using the Wilbur and Lipman algorithm (window: 10; K-tuple: 7; gap penalty: 3) as described by Wilbur and Lipman in Proc. Natl. Acad. Sci. USA 80: 726–730 (1983), specifically incorporated herein by reference. The U3-R junction in HIV-1 is indicated and the poly A addition signal and potential TATA promoter regions are boxed. In FIG. 1B, the symbols 3, H, Ps and Pv refer to the restriction sites BamHI, HindIII, PstI and PvuII, respectively.

FIG. 3 generally depicts a restriction map of the HIV-2 ROD genome and its homology to HIV-1. In FIG. 3A, the open boxes represent viral sequences, the LTR are filled, and the dotted boxes represent cellular flanking sequences (not mapped). Only some characteristic restriction enzyme sites are indicated. λROD 27 and λROD 35 are derived from integrated proviruses while ROD 4 is derived from a circular viral DNA. The portion of the lambda clones that hybridzes to the CDNA E2 is indicated below the maps. A restriction map of the λROD isolate was re-constructed from these three lambda clones. In this map, the re-striction sites are identified as follows: B: BamHI; E: EcoRI; H: HindIII; K: KpnI; Ps: PstI; Pv: PvuII; S: SacI; X: XbaI. R and L are the right and left BamHI arms of the lambda L47.1 vector.

FIG. 4 generally depicts the restriction map polymorphism in different HIV-2 isolates and shows comparison of HIV-2 to SIV.

FIG. 6 depicts the nucleotide sequence encoding the pol gene, which corresponds to nucleotides 1829–4936 of the Sequence set forth at pages 24–34, and the corresponding amino acid sequence.

DETAILED DESCRIPTION OF THE PREFERRED EMBODIMENTS

Figure 2A:
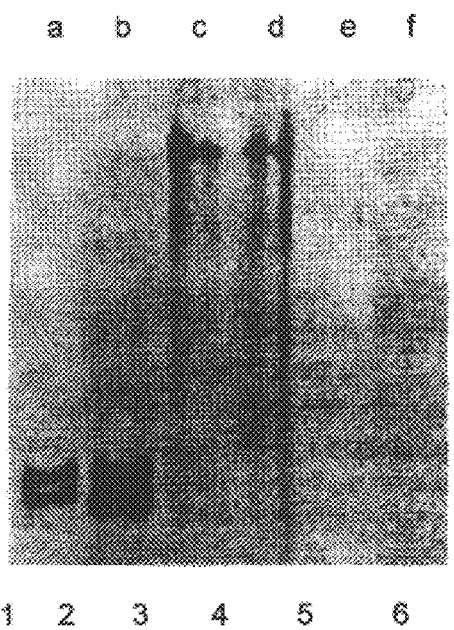
FIG. 2A and a specifically depict a Southern blot of DNA extracted from CEM cells infected with the following isolates: HIV-2$_{ROD}$ (a,c), HIV-2$_{DUL}$ (b,d), and HIV-1$_{BRU}$ (e,f). DNA in lanes a,b,f was Pst I digested; in c,d,e DNA was undigested.
Figure 2B:
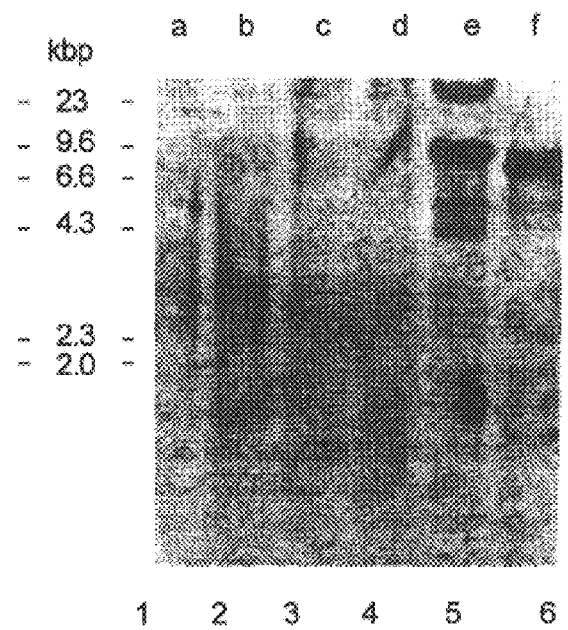
FIG. 2 generally depicts the HIV-2 specificity of the E2 clone.
FIGS. 2C and D specifically depict dot blot hybridization of pelleted virions from CEM cells infected by the HIV-1$_{BRU}$ (1), Simian Immunodeficiency Virus (SIV) isolate Mm 142-83 (3), HIV-2$_{DUL}$ (4), HIV-2$_{ROD}$ (5), and HIV-1$_{ELI}$ (6). Dot 2 is a pellet from an equivalent volume of supernatant from uninfected CEM. Thus, FIG. 2A and C depicts hybridization with the HIV-2 ONA (E2) and FIG. 2B and D depicts hybridization to an HIV-1 probe consisting of a 9Kb SacI insert from HIV-1 BRU(clone lambda J 19).
Figure 2C:
Figure 2D:
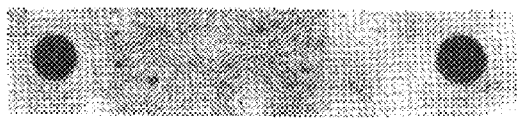

Reference will now be made in detail to the presently preferred embodiments of the invention, which, together with the following examples, serve to explain the principles of the invention.

The genetic structure of the HIV-2 virus has been analyzed by molecular cloning according to the method set forth herein and in the Examples. A restriction map of the genome of this virus is included in FIG. 4. In addition, the partial sequence of a cDNA complementary to the genomic RNA of the virus has been determined. This cDNA sequence information is included in FIG. 1.

Also contained herein is data describing the molecular cloning of the complete 9.5 kb genome of HIV-2, data describing the observation of restriction map polymorphism between different isolates, and an analysis of the relationship between HIV-2 and other human and simian retroviruses. From the totality of these data, diagnostic probes can be discerned and prepared.

Generally, to practice one embodiment of the present invention, a series of filter hybridizations of the HIV-2 RNA genome with probes derived from the complete cloned HIV-1 genome and from the qaq and pol genes were conducted. These hybridizations yielded only extremely weak signals even in conditions of very low stringency of hybrization and washing. Thus, it was found to be difficult to assess the amount of HIV-2 viral and proviral DNA in infected cells by Southern blot techniques.

Therefore, a complementary DNA (cDNA) to the HIV-2 genomic RNA initially was cloned in order to provide a specific hybridization probe. To construct this cDNA, an oligo (dT) primed cDNA first-strand was made in a detergent-activated endogenous reaction using HIV-2 reverse transcriptase with virions purified from supernatants of infected CEM cells. The CEM cell line is a lymphoblastoid CD4+ cell line described by G. E. Foley et al. in Cancer 18: 522–529 (1965), specifically incorporated herein by reference. The CEM cells used were infected with the isolate ROD and were continuously producing high amounts of HIV-2.

After second-strand synthesis, the cDNAs were inserted into the M 13 tg 130 bacteriophage vector. A collection of $10^4$ M13 recombinant phages was obtained and screened in situ with an HIV-1 probe spanning 1.5 kb. of the 3' end of the $LAV_{BRU}$ isolate (depicted in FIG. 1A). Some 50 positive plaques were detected, purified, and characterized by end sequencing and cross-hybridizing the inserts. This procedure is described in more detail in Example 1 and in FIG. 1.

The different clones were found to be complementary to the 3' end of a polyadenylated RNA having the AATAAA signal about 20 nucleotides upstream of the poly A tail, as found in the long terminal repeat (LTR) of HIV-1. The LTR region of HIV-1 has been described by S. Wain Hobson et al. in Cell 40: 9–17 (1985), specifically incorporated herein by reference. The portion of the HIV-2 LTR that was sequenced was related only distantly to the homologous domain in HIV-1 as demonstrated in FIG. 1 B. Indeed, only about 50% of the nucleotides could be aligned and about a hundred insertions/deletions need to be introduced. In comparison, the homology of the corresponding domains in HIV-1 isolates from USA and Africa is greater than 95% and no insertions or deletions are seen.

The largest insert of this group of M13 clones was a 2 kb. clone designated E2. Clone E2 was used as a probe to demonstrate its HIV-2 specificity in a series of filter hybridization experiments. Firstly, this probe could detect the genomic RNA of HIV-2 but not HIV-1 in stringent conditions as shown in FIG. 2, C and D. Secondly, positive signals were detected in Southern blots of DNA from cells infected with the ROD isolate as well as other isolates of HIV-2 as shown in FIG. 2, A and FIG. 4, A. No signal was detected with DNA from uninfected cells or HIV-1 infected cells, confirming the exogenous nature of HIV-2. In undigested DNA from HIV-2 infected cells, an approximately 10 kb. species, probably corresponding to linear unintegrated viral DNA, was principally detected along with a species with an apparent size of 6 kb., likely to be the circular form of the viral DNA. Conversely, rehybridization of the same filter with an HIV-1 probe under stringent conditions showed hybridization to HIV-1 infected cells only as depicted in FIG. 2, B.

To isolate the remainder of the genome of HIV-2, a genomic library in lambda phage L47.1 was constructed. Lambda phage L47.1 has been described by W. A. M. Loenen et al. in Gene 10: 249–259 (1980), specifically incorporated herein by reference. The genomic library was constructed with a partial Sau3AI restriction digest of the DNA from the CEM cell line infected with HIV-$2_{ROD}$.

About $2\times10^6$ recombinant plaques were screened in situ with labelled insert from the E2 cDNA clone. Ten recombinant phages were detected and plaque purified. Of these phages, three were characterized by restriction mapping and Southern blot hybridization with the E2 insert and probes from its 3' end (LTR) or 5' end (envelope), as well as with HIV-1 subgenomic probes. In this instance, HIV-1 probes were used under non-stringent conditions.

Figures 3A, 3B:
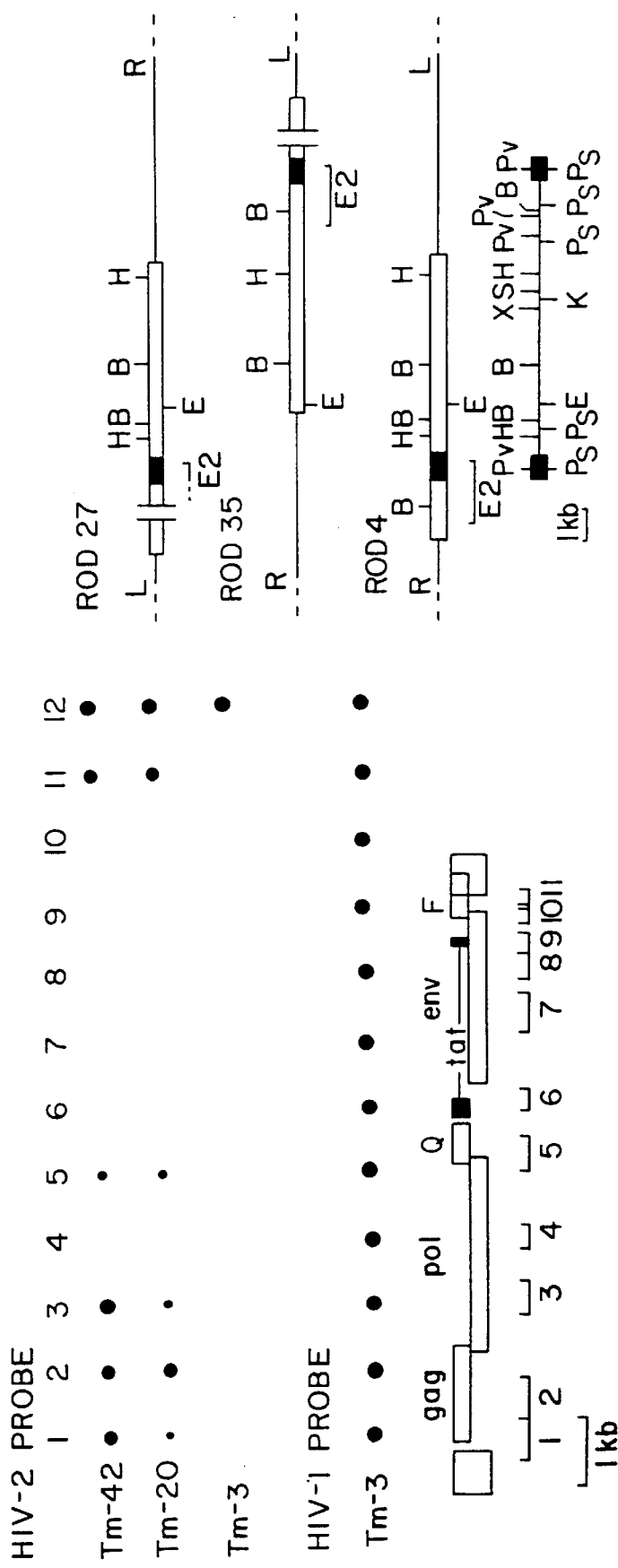
FIG. 3A specifically depicts the organization of three recombinant phage lambda clones, ROD 4, ROD 27, and ROD 35.
FIG. 3B specifically depicts dots 1-11 which correspond to the single-stranded DNA form of M13 subclones from the HIV-1$_{BRU}$ cloned genome (λJ19). Their size and position on the HIV-1 genome, determined by sequencing is shown below the figure. Dot 12 is a control containing lambda phage DNA. The dot-blot was hybridized in low stringency conditions as described in Example 1 with the complete lambda λROD 4 clone as a probe, and successively washed in 2×SSC, 0.1% SDS at 25° C. (Tm −42° C.), 1×SSC, 0.1% SDS at 60° C. (Tm −20° C.), and 0.1×SSC, 0.1% SDS at 60° C. (Tm −3° C.) and exposed overnight. A duplicate dot blot was hybridized and washed in stringent conditions (as described in Example 2) with the labelled lambda J19 clone carrying the complete HIV-1$_{BRU}$ genome. HIV-1 and HIV-2 probes were labelled the same specific activity ($10^8$ cpm/g.).
Figure 4A:
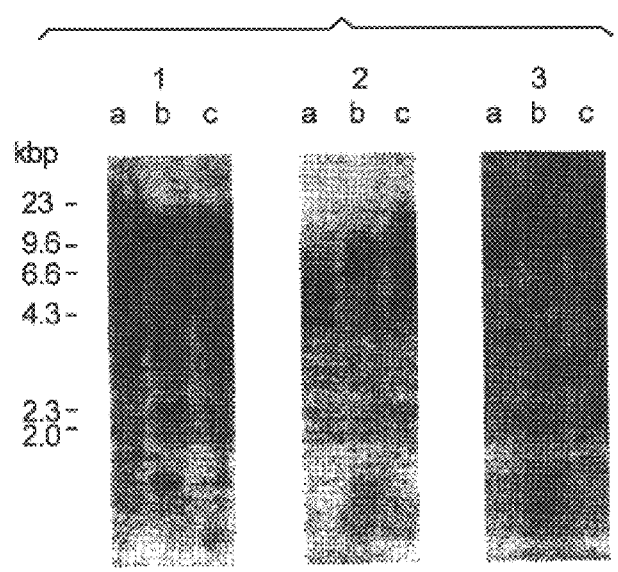
FIG. 4A specifically depicts DNA (20 ug. per lane) from CEM cells infected by the isolate HIV-2$_{DUL}$ (panel 1) or peripheral blood lymphocytes (PBL) infected by the isolates HIV-2$_{GOM}$ (panel 2) and HIV-2$_{MIR}$ (panel 3) digested with: EcoRI (a), PstI (b), and HindIII (c). Much less viral DNA was obtained with HIV-2 isolates propagated on PBL. Hybridization and washing were in stringent conditions, as described in Example 2, with $10^6$ cpm/ml. of each of the E2 insert (cDNA) and the 5 kb. HindIII fragment of λROD 4, labelled to $10^9$ cpm/ug.
Figure 4B:
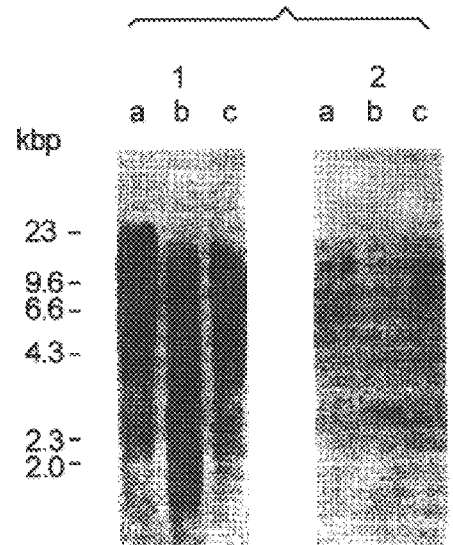
FIG. 4B specifically depicts DNA from HUT 78 (a human T lymphoid cell line) cells infected with STLV3 MAC isolate Mm 142-83. The same amounts of DNA and enzymes were used as indicated in panel A. Hybridization was performed with the same probe as in A, but in non-stringent conditions. As described in Example 1 washing was for one hour in 2×SSC, 0.1% SDS at 40° C. (panel 1) and after exposure, the same filter was re-washed in 0.1× SSC, 0.1% SDS at 60° C. (panel 2). The autoradiographs were obtained after overnight exposition with intensifying screens.
Figure 3A:
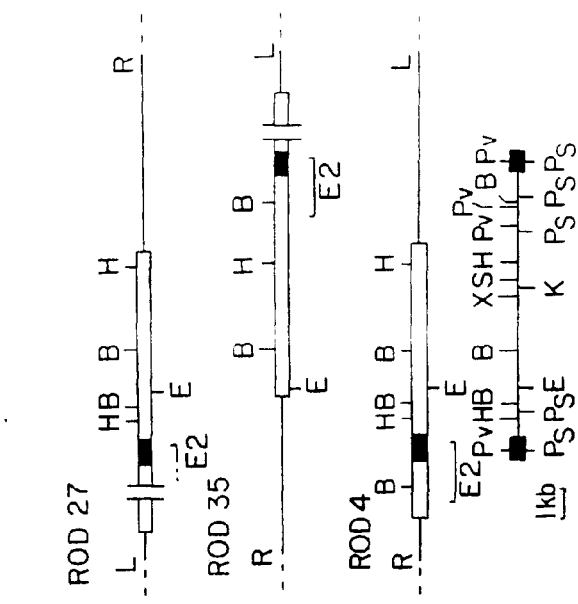
Figure 3B:
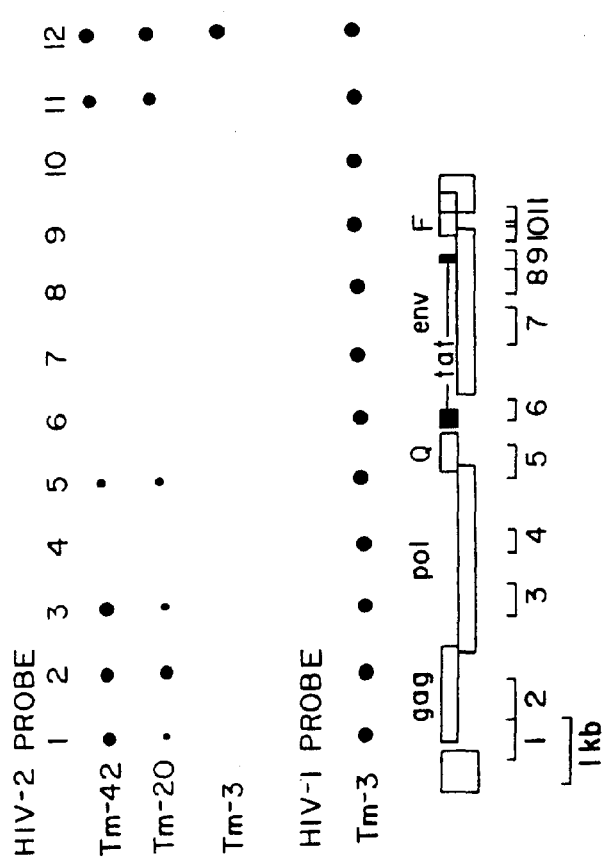
Figure 4A:
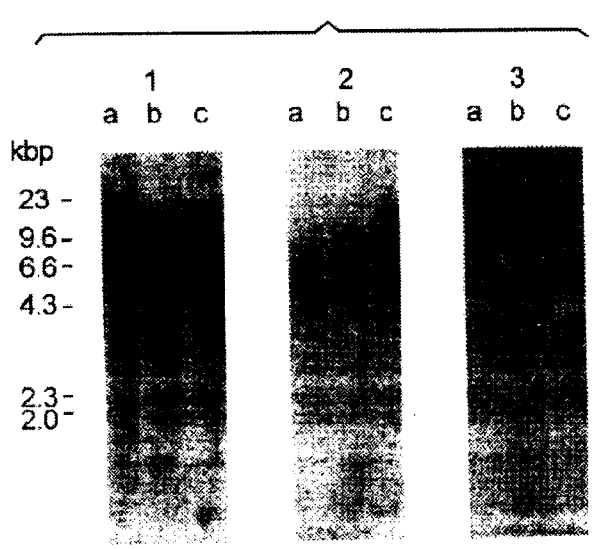
Figure 4B:
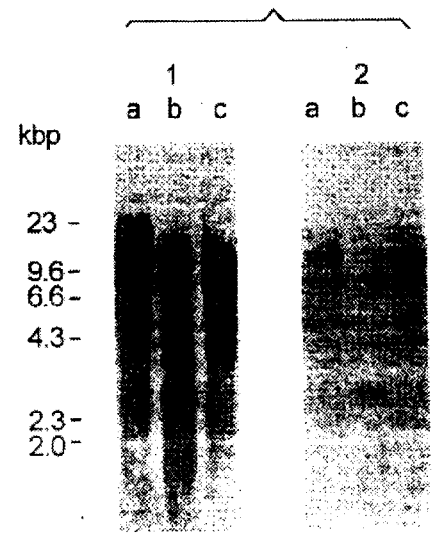

A clone carrying a 9.5 kb. insert and derived from a circular viral DNA was identified as containing the complete genome and designated λROD 4. Two other clones, λROD 27 and λROD 35 were derived from integrated proviruses and found to carry an LTR and cellular flanking sequences and a portion of the viral coding sequences as shown in FIG. 3, A.

Fragments of the lambda clones were subcloned into a plasmid vector p UC 18.

Plasmid pROD 27-5' is derived from λROD 27 and contains the 5' 2Kb of the HIV-2 genome and cellular flanking sequences (5' LTR and 5' viral coding sequences to the EcoRI site) Plasmid p ROD 4-8 is derived from λROD 4 and contains the about 5Kb HindIII fragment that is the central part of the HIV-2 genome.

Plasmid pROD 27-5' and p ROD 4.8 inserts overlap.

Plasmid pROD 4.7 contains a HindIII 1.8 Kb fragment from λROD 4. This fragment is located 3' to the fragment subcloned into pROD 4.8 and contains about 0.8 Kb of viral coding sequences and the part of the Lambda phage (λL47.1) left arm located between the BamHl and HindIII cloning sites.

Plasmid pROD 35 contains all the HIV-2 coding sequences 3' to the EcoRI site, the 3' LTR and about 4 Kb of cellular flanking sequences.

Figure 5:
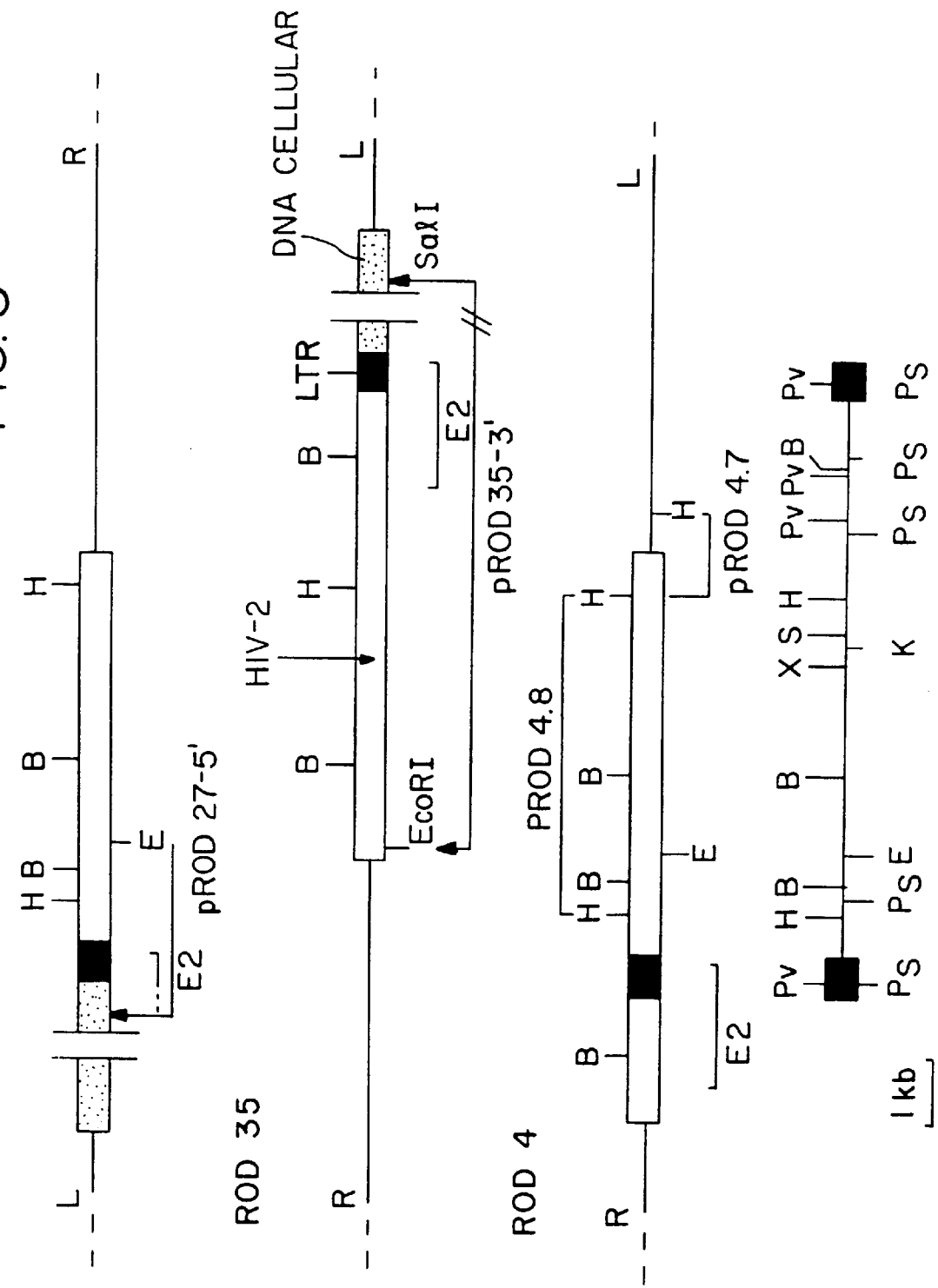
FIG. 5 depicts the position of derived plasmids from λROD 27, λROD 35 and λROD 4.
Figure 2A:
Figure 2B:
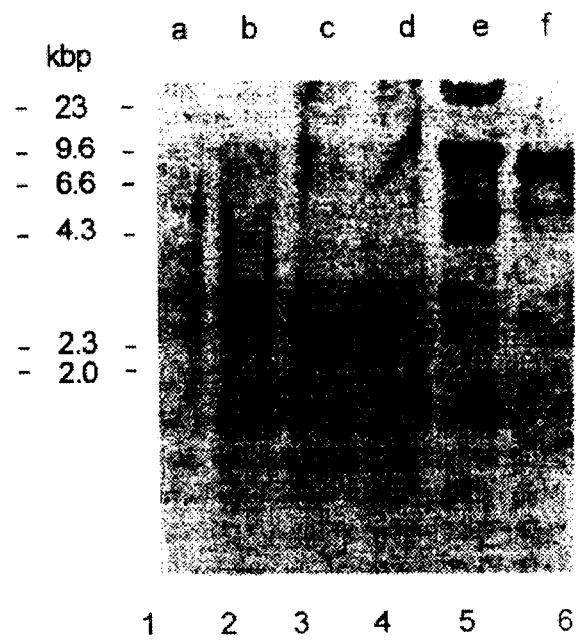
Figure 2C:
Figure 2D:

Plasmid pROD 27-5' and pROD 35 in E. coli strain HB 101 are deposited respectively under No. 1–626 and 1–633 at the CNCM, and have also been deposited at the NCIB (British Collection). These plasmids are depicted in FIG. 5. Plasmids pROD 4–7 and pROD 4–8 in E. coli strain TGl are deposited respectively under No. 1–627 and 1–628 at the CNCM.

To reconstitute the complete HIV-2 ROD genome, pROD 35 is linearized with EcoRI and the EcoRI insert of pROD 27-5' is ligated in the correct orientation into this site.

The relationship of HIV-2 to other human and simian retroviruses was surmised from hybridization experiments. The relative homology of the different regions of the HIV-1 and 2 genomes was determined by hybridization of fragments of the cloned HIV-1 genome with the labelled λROD 4 expected to contain the complete HIV-2 genome (FIG. 3, B). Even in very low stringency conditions (Tm-42° C.), the hybridization of HIV-1 and 2 was restricted to a fraction of their genomes, principally the qaq gene (dots 1 and 2), the reverse transcriptase domain in pol (dot 3), the end of pod and the Q (or sor) genes (dot 5) and the F gene (or 3' orf) and 3' LTR (dot 11). The HIV-1 fragment used to detect the HIV-2 cDNA clones contained the dot 11 subclone, which hybridized well to HIV-2 under non-stringent conditions. Only the signal from dot 5 persisted after stringent washing. The envelope gene, the region of the tat gene and a part of pol thus seemed very divergent. These data, along with the LTR sequence obtained (FIG. 1, B), indicated that HIV-2 is not an envelope variant of HIV-1, as are African isolates from Zaire described by Alizon et al., Cell 40:63–74 (1986).

It was observed that HIV-2 is related more closely to the Simian Immunodeficiency Virus (SIV) than it is to HIV-1. This correlation has been described by F. Clavel et al. in C.R. Acad. Sci. (Paris) 302: 485–488 (1986) and F. Clavel et al. in Science 233: 343–346 (1986), both of which are specifically incorporated herein by reference. Simian Immunodeficiency Virus (also designated Simian T-cell Lymphotropic Virus Type 3, STLV-3) is a retrovirus first isolated from captive macaques with an AIDS-like disease in the USA. This simian virus has been described by M. D. Daniel et al. in Science 228: 1201–1204 (1985), specifically in corporated herein by reference.

All the SIV proteins, including the envelope, are immune precipitated by sera from HIV-2 infected patients, whereas the serological cross-reactivity of HIV-1 to 2 is restricted to core proteins. However SIv and HIV-2 can be distinguished by slight differences in the apparent molecular weight of their proteins.

In terms of nucleotide sequence, it also appears that HIV-2 is closely related to SIV. The genomic RNA of SIV can be detected in stringent conditions as shown in FIG. 2, C by HIV. probes corresponding to the LTR and 3' end of the genome (E2) or to the qaq or gol genes. Under the same conditions, HIV-1 derived probes do not detect the SIV genome as shown in FIG. 2, D.

In Southern blots of DNA from SIV-infected cells, a restriction pattern clearly different from HIV-2$_{ROD}$ and other isolates is seen. All the bands persist after a stringent washing, even though the signal is considerably weakened, indicating a sequence homology throughout the genomes of HIV-2 and SIV. It has recently been shown that baboons and macaques could be infected experimentally by HIV-2, thereby providing an interesting animal model for the study of the HIV infection and its preventive therapy. Indeed, attempts to infect non-human primates with HIV-1 have been successful only in chimpanzees, which are not a convenient model.

From an initial survey of the restriction maps for certain of the HIV-2 isolates obtained according to the methods described herein, it is already apparent that HIV-2, like HIV-1, undergoes restriction site polymorphism. FIG. 4 A depicts examples of such differences for three isolates, all different one from another and from the cloned HIV-2$_{ROD}$. It is very likely that these differences at the nucleotide level are accompanied by variations in the amino-acid sequence of the viral proteins, as evidenced in the case of HIV-1 and described by M. Alizon et al. in Cell 46: 63–74 (1986), specifically incorporated herein by reference. It is also to be expected that the various isolates of HIV-2 will exhibit amino acid heterogeneities. See, for example, Clavel et al., Nature 324 (18):691–695 (1986), specifically incorporated herein by reference.

Further, the chacterization of HIV-2 will also delineate the domain of the envelope glycoprotein that is responsible for the binding of the surface of the target cells and the subsequent internalization of the virus. This interaction was shown to be mediated by the CD4 molecule itself in the case of HIV-1 and similar studies tend to indicate that HIV-2 uses the same receptor. Thus, although there is wide divergence between the env genes of HIV-1 and 2, small homologous domains of the envelopes of the two HIV could represent a candidate receptor binding site. This site could be used to raise a protective immune response against this group of retroviruses.

From the data discussed herein, certain nucleotide sequences have been identified which are capable of being used as probes in diagnostic methods to obtain the immunological reagents necessary to diagnose an HIV-2 infection. In particular, these sequences may be used as probes in hybridization reactions with the genetic material of infected patients to indicate whether the RNA of the HIV-2 virus is present in these patient's lymphocytes or whether an analogous DNA is present. In this embodiment, the test methods which may be utilized include Northern blots, Southern blots and dot blots. One particular nucleotide sequence which may be useful as a probe is the combination of the 5 kb. HindIII fragment of ROD 4 and the E2 cDNA used in FIG. 4.

In addition, the genetic sequences of the HIV-2 virus may be used to create the polypeptides encoded by these sequences. Specifically, these polypeptides may be created by expression of the cDNA obtained according to the teachings herein in hosts such as bacteria, yeast or animal cells. These polypeptides may be used in diagnostic tests such as immunofluorescence assays (IFA), radioimmunoassays (RIA) and Western Blot tests.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

In addition, monoclonal antibodies to these polypeptides or fragments thereof may be created. The monoclonal antibodies may be used in immunodiagnostic tests in an analogous manner as the polypeptides described above.

The polypeptides of the present invention may also be used as immunogenic reagents to induce protection against infection HIV-2 viruses. In this embodiment, the polypeptides produced by recombinant-DNA techniques would function as vaccine agents.

Also, the polypeptides of this invention may be used in competitive assays to test the ability of various antiviral agents to determine their ability to prevent the virus from fixing on its target.

Thus, it is to be understood that application of the teachings of the present invention to a specific problem or environment will be within the capabilities of one having ordinary skill in the art in light of the teachings contained herein. Examples of the products of the present invention and representative pro- cesses for their isolation and manufacture appear above and in the following examples.

EXAMPLES

Example 1

Cloning of a cDNA Complementary to Genomic RNA From HIV-2 Virions

HIV-2 virions were purified from 5 liters of supernatant from a culture of the CEM cell line infected with the ROD isolate and a cDNA first strand using oligo (dT) primer was synthesized in detergent activated endogenous reaction on pelleted virus, as described by M. Alizon et al. in Nature, 312: 757–760 (1984), specifically incorporated herein by reference. RNA-cDNA hybrids were purified by phenol-chloroform extraction and ethanol precipitation. The second-strand cDNA was created by the DNA polymerase I/RNAase H method of Gubler and Hoffman in Gene, 25: 263–269 (1983), specifically incorporated herein by reference, using a commercial CDNA synthesis kit obtained from Amersham. After attachment of EcoRI linkers (obtained from Pharmacia), EcoRI digestion, and ligation into EcoRI-digested dephosphorylated M13 tg 130 vector (obtained from Amersham), a cDNA library was obtained by transformation of the *E. coli* TGI strain. Recombinant plaques ($10^4$) were screened in situ on replica filters with the 1.5 kb. HindIII fragment from clone J19, corresponding to the 3' part of the genome of the LAVBRU isolate of HIV-1, $^{32}$p labelled to a specific activity of $10^9$ cpm ug. The filters were prehybridized in 5×SSC, 5×Denhardt solution, 25% formamide, and denatured salmon sperm DNA (100 ug/ml.) at 37° C. for 4 hours and hybridized for 16 hours in the same buffer (Tm-42° C.) plus $4×10^7$ cpm of the labelled probe ($10^6$ cpm/ml. of hybridization buffer). The washing was done in 5×SSC, 0.1% SDS at 25° C. for 2 hours. 20×SSC is 3M NaCl, 0.3M Na citrate. Positive plaques were purified and single-stranded M13 DNA prepared and end-sequenced according to the method described in Proc. Nat'l. Acad. Sci. USA, 74: 5463–5467 (1977) of Sanger et al.

Example 2

Hybridization of DNA from HIV-1 and HIV-2 Infected Cells and RNA from HIV-1 and 2 and SIV Virons With a Probe Derived From an HIV-2 Cloned cDNA DNA was extracted from infected CEM cells continuously producing HIV-1 or 2. The DNA digested with 20 ug of PstI digested with or undigested, was electrophoresed on a 0.8% agarose gel, and Southern-transferred to nylon membrane. Virion dot-blots were prepared in duplicate, as described by F. Clavel et al. in Science 233: 343–346 (1986), specifically incorporated herein by reference, by pelleting volumes of supernatant corresponding the same amount of reverse transcriptase activity. Prehybridization was done in 50% formamide, 5×SSC, 5×Denhardt solution, and 100 ug./ml. denatured salmon sperm DNA for 4 hours at 42° C. Hybridization was performed in the same buffer plus 10% Dextran sulphate, and $10^6$ cpm/nl. of the labelled E2 insert (specific activity $10^9$ cpm/ug.) for 16 hours at 42° C. Washing was in 0.1×SSC, 0.1% SDS for 2×30 mn. After exposition for 16 hours with intensifying screens, the Southern blot was dehybridized in 0.4 N NaOH, neutralized, and rehybridized in the same conditions to the HIV-1 probe labelled to $10^9$ cpm/ug.

Example 3

Cloning in Lambda Phage of the Complete Provirus DNA of HIV-2

DNA from the HIV-2ROD infected CEM (FIG. 2, lanes a and c) was partially digested with Sau3AI. The 9–15 kb. fraction was selected on a 5–40% sucrose gradient and ligated to BamHI arms of the lambda L47.1 vector. Plaques ($2×10^6$) obtained after in vitro packaging and plating on *E. coli* LA 101 strain were screened in situ with the insert from the E2 cDNA clone. Approximately 10 positive clones were plaque purified and propagated on *E. coli* C600 recBC. The ROD 4, 27, and 35 clones were amplified and their DNA characterized by restriction mapping and Southern blotting with the HIV-2 CDNA clone under stringent conditions, and gag-pol probes from HIV-1 used under non stringent conditions.

Example 4

Complete Genomic Sequence of the ROD HIV-2 Isolate

Experimental analysis of the HIV-2 ROD isolate yielded the following sequence which represents the complete genome of this HIV-2 isolate. Genes and major expression products identified within the following sequence are indicated by nucleotides numbered below:

1) GAG gene (546–2111) expresses a protein product having a molecular weight of around 55Kd and is cleaved into the following proteins:
   a) p 16 (546–950)
   b) p 26 (951–1640)
   c) p 12 (1701–2111)
2) polymerase (1829–4936)
3) Q protein (4869–5513)
4) R protein (5682–5996)
5) X protein (5344–5679)
6) Y protein (5682–5996)
7) Env protein (6147–8720)
8) F protein (8557–9324)
9) TAT gene (5845–6140 and 8307–8400) is expressed by two exons separated by introns.
10) ART protein (6071–6140 and 8307–8536) is similarly the expression product of two exons.
11) LTR:R (1–173 and 9498–9671)
12) U5 (174–299)
13) U3 (8942–9497)

It will be known to one of skill in the art that the absolute numbering which has been adopted is not essential. For example, the nucleotide within the LTR which is designated as "1", is a somewhat arbitrary choice. What is important is the sequence information provided.

```
GGTCGCTCTGCGGAGAGGCTGGCAGATTGAGCCCTGGGAGGTTCTCTCCAGCACTAGCAG
    *         *         *         *         *         *
GTAGAGCCTGGGTGTTCCCTGCTAGACTCTCACCAGCACTTGGCCGGTGCTGGGCAGACG
    *         *        100        *         *         *
GCCCCACGCTTGCTTGCTTAAAAACCTCTTAATAAAGCTGCCAGTTAGAAGCAAGTTAAG
    *         *         *         *         *         *
TGTGTGCTCCCATCTCTCCTAGTCGCCGCCTGGTCATTCGGTGTTCACCTGAGTAACAAG
    *        200        *         *         *         *
ACCCTGGTCTGTTAGGACCCTTCTTGCTTTGGGAAACCGAGGCAGGAAAATCCCTAGCAG
    *         *         *         *         *        300
```

-continued

```
GTTGGCGCCTGAACAGGGACTTGAAGAAGACTGAGAAGTCTTGGAACACGGCTGAGTGAA
     *         *         *         *         *         *
GGCAGTAAGGGCGGCAGGAACAAACCAAACCACGACGGAGTGCTCCTAGAAAGGCGCGAG
     *         *         *    400  *         *         *
GTACCAAAGGCAGCGTGTGGAGCGGGAGGAGAAGAGGCCTCCGGGTGAAGGTAAGTACCT
     *         *         *         *         *         *
ACACCAAAAACTGTAGCCGAAAGGGCTTGCTATCCTACCTTTAGACAGGTAGAAGATTGT
     *         *    500  *         *         *         *
             MetGlyAlaArgAsnSerValLeuArgGlyLysLysAlaAspGluLeuGluArgIle
GGGAGATGGGCGCGAGAAACTCCGTCTTGAGAGGGAAAAAAGCAGATGAATTAGAAAGAA
     *         *         *         *         *    600
ArgLeuArgProGlyGlyLysLysLysTyrArgLeuLysHisIleValTrpAlaAlaAsn
TCAGGTTACGGCCCGGCCGAAAGAAAAAGTACAGGCTAAAACATAtTGTGTGGGCAGCGA
     *         *         *         *         *         *
LysLeuAspArgPheGlyLeuAlaGluSerLeuLeuGluSerLysGluGlyCyeGlnLys
ATAAATTGGACAGATTCGGATTACCAGAGAGCCTGTTGGAGTCAAAAGAGGGTTGTCAAA
     *         *         *    700  *         *         *
IleLeuThrValLeuAspProMetValProThrGlySerGluAsnLeuLysSerLeuPhe
AAATTCTTACAGTTTTAGATCCAATGGTACCGACAGGTTCAGAAAATTTAAAAAGTCTTT
     *         *         *         *         *         *
AsnThrValCysValIleTrpCysIleHisAlaGluGluLysValLysAspThrGluGly
TTAATACTGTCTGCGTCATTTGGTGCATACACGCAGAAGAGAAAGTGAAACATACTGAAG
     *         *    800  *         *         *         *
AlaLysGlnIleValArgArgHisLeuValAlaGluThrGlyThrAlaGluLysMetPro
GAGCAAAACAAATAGTGCGGAGACATCTAGTGGCAGAAACAGGAACTGCAGACAAAATGC
     *         *         *         *         *    900
SerThrSerArgProThrAlaProSerSerGluLysGlyGlyAsnTyrProValGlnHis
CAAGCACAAGTAGACCAACAGCACCATCTAGCGAGAAGGGAGGAAATTACCCAGTGCAAC
     *         *         *         *         *         *
ValGlyGlyAsnTyrThrHisIleProLeuSerProArgThrLeuAsnAlaTrpValLys
ATGTACGCGGCAACTACACCCATATACCGCTCAGTCCCCGAACCCTAAATGCCTGGGTAA
     *         *         *   1000  *         *         *
LeuValGluGluLysLysPheGlyAlaGluValValProGlyPheGlnAlaLeuSerGlu
AATTAGTAGAGGAAAAAAAGTTCGGGGCAGAAGTAGTGCCAGGATTTCAGGCACTCTCAG
     *         *         *         *         *         *
GlyCysThrProTyrAspIleAsnGlnMetLeuAsnCysValglyAspHisGlnAlaAla
AAGGCTGCACGCCCTATGATATCAACCAAATGCTTAATTGTGTGGGGACCATCAAGCAG
     *         *   1100  *         *         *         *
MetGlnIleIleArgGluIleIleAsnGluGluAlaAlaGluTrpAspValGlnHisPro
CCATGCAGATAATCAGGGAGATTATCAATGGGAAGCATGCAGAATGGGATGTGCAACATC
     *         *         *         *         *   1200
IleProGlyProLeuProAlaGlyGlnLeuArgGluProArgGlySerAspIleAlaGly
CAATACCAGGCCCCTTACCAGCGGGGCAGCTTAGAGAGCCAAGGGGATCTCGACATAGCAG
     *         *         *         *         *         *
    ThrThrSerThrValGluGluGlnIleGlnTrpMetPheAtgProGlnAsnProValPro
CGACAACAAGCACAGTAGAAGAACAGATCCAGTGGATGTTTAGGCCACAAAATCCTGTAC
     *         *         *   1300  *         *         *
     ValGlyAsnIleTyrArgArgTrpIleGlnIleGlyLeuGlnLysCysValArgMetTyr
CACTAGGAAACATCTATAGAAGATGGATCCAGATAGGATTGCAGAAGTGTGTCAGGATGT
     *         *         *         *         *         *
     AsnProThrAsnIleLeuAspIleLysGlnGlyProLysGluProPheGlnSerTyrVal
ACAACCCGACCAACATCCTAGACATAAAACAGGGACCAAAGGAGCCGTTCCAAAGCTATG
     *         *   1400  *         *         *         *
AspArgPheTyrLysSerLeuArgAlaGluGlnThrAspProAlaValLysAsnTrpMet
TAGATAGATTCTACAAAAGCTTGAGGGCAGAACAAACAGATCCAGCAGTGAAGAATTGGA
     *         *         *         *         *   1500
     ThrGlnThrLeuLeuValGlnAsnAlaAsnProAspCysLysLeuValLeuLysGlyLeu
TGACCCAAACACTGCTAGTACAAAATGCCAACCCAGACTGTAAATTAGTGCTAAAAGGAC
     *         *         *         *         *         *
     GlyMetAsnProThrLeuGluGluMetLeuThrAlaCysGlnGlyValGlyGlyProGly
TAGGGATGAACCCTACCTTAGAAGAGATGCTGACCGCCTGTCAGGGGGTAGGTGGGCCAG
     *         *         *   1600  *         *         *
     GlnLysAlaArgLeuMetAlaGluAlaLeuLysGluValIleGlyProAlaProIlePro
GCCAGAAAGCTAGATTAATGGCAGAGGCCCTGAAAGAGGTCATAGGACCTGCCCCTATCC
     *         *         *         *         *         *
     PheAlaAlaAlaGlnGlnArgLysAlaPheLysCusTrpAsnCysGlyLysGluGlyHis
CATTCGCAGCAGCCCAGCAGAGAAAGGCATTTAAATGCTGCAACTGTGGAAAGGAAGGGC
     *         *   1700  *         *         *         *
     SerAlaArgGlnCysArgAlaProArgArgGlnGlyCysTrpLysCysGlyLysProGly
ACTCGGCAAGACAATGCCGAGCACCTAGAAGGCAGGGCTGCTGGAAGTGTGGTAAGCCAG
     *         *         *         *         *   1800
                   ThrGlyArgPhePheArgThrGlyProLeuGly
     HisIleMetThrAsnCysProAspArgGlnAlaGlyPheLeuGlyLeuGleProTrpGly
GACACATCATGACAAACTGCCCAGATAGACAGGCAGGTTTTTTAGGACTGGGCCCTTGGG
     *         *         *         *         *         *
     LysGluAlaProGlnLeuProArgGlyProSerSerAlaGlyAlaAspThrAsnSerThr
     LysLysProArgAsnPheProValAlaGlnValProGlnGlyLeuThrProThrAlaPro
GAAAGAAGCCCCGCAACTTCCCCGTGGCCCAAGTTCCGCAGGGGCTGACACCAACAGCAC
     *         *         *   1900  *         *         *
     ProSerGlySerSerSerGlySerThrGlyGluIleTyrAlaAlaArgGluLysThrGlu
```

-continued

```
ProValAspProAlaValAspLeuLeuGluLysTyrMetGlnGlnGlyLysArgGlnArg
CCCCAGTGGATCCAGCAGTGGATCTACTGGAGAAATATATGCAGCAAGGGAAAAGACAGA
         *         *         *         *         *         *
ArgAlaGluArgGluThrIleGlnGlySerAspArgGlyLeuThrAlaProArgAlaGly
   GluGlnArgGluArgProTyrLysGluValThrGluAspLeuLeuHisLeuGluGlnGly
GAGAGCAGAGAGAGAGACCATACAAGGAAGTGACAGAGGCTTACTGCACCTGCGAGCAGG
         *       2000        *         *         *         *
   GlyAspThrIlegInGlyAlaThrAsnArgGlyLeuAlaAlaProGlnPheSerLeuTrp
   GluThrProTyrArgGluProProThrGluAspLeuLeuHisLerAsnSerLeuPheGly
GGGAGACACCATACAGGGAGCCAACCACAGAGGACTTGCTGCACCTCAATTCTCTCTTTG
         *         *         *         *         *       2100
  LysArgProValValThrAlaTyrIleGluGlyGlnProValGluValLeuLeuAspThr
  LysAspGla
GAAAAGACCAGTAGTCACAGCATACATTGAGGGTCAGCCAGTAGAAGTCTTGTTAGACAC
         *         *         *         *         *         *
   GlyAlaAspAspSerIleValAlaGlyIleGluLeuGlyAsnAsnTyrSerProLysIle
AGGGGCTGACGACTCAATAGTAGCAGGAATAGAGTTAGGGAACAATTATAGCCCAAAAAT
         *         *       2200        *         *         *
   ValGlyGlyIleGlyGlyPheIleAsnThrLysGluTyrLysAsnValGluIleGluVal
AGTAGGGGGAATAGGGGGATTCATAAATACCAAGGAATATAAAAATGTAGAAATAGAAGT
         *         *         *         *         *         *
  LeuAsnLysLysValArgAlaThrIleMetThrGlyAspThrProIleAsnIlePheGly
TCTAAATAAAAAGGTACGGGCCACCATAATGACAGGCGACACCCCAATCAACATTTTTGG
         *       2300        *         *         *         *
   ArgAsnIleLeuThrAlaLeuGlyMetSerLeuAsnLeuProValAlaLysValGluPro
CAGAAATATTCTGACAGCCTTAGGCATGTCATTAAATCTACCAGTCGCCAAAGTAGAGCC
         *         *         *         *         *       2400
  IleLysIleMetLeuLysProGlyLysAspGlyProLysLeuArgGlnTrpProLeuThr
AATAAAAATAATGCTAAAGCCAGGGAAAGATGGACCAAAACTGAGACAATGGCCCTTAAC
         *         *         *         *         *         *
  LysGluLysIleGluAlaLeuLysGluIleCysGluLysMetGluLysGluGlyGlnLeu
AAAAGAAAAATAGAAGCACTAAAAGAAATCTGTGAAAAAATGGAAAAAGAAGGCCAGCT
         *         *       2500        *         *         *
  GluGluAlaProProThrAsnProTyrAsnThrProThrPheAlaIleLysLysLysAsp
AGAGGAAGCACCTCCAACTAATCCTTATAATACCCCCACATTTGCAATCAAGAAAAAGGA
         *         *         *         *         *         *
  LysAsnLysTrpArgMetLeuIleAspPheArgGluLeuAsnLysValThrGlnAspPhe
CAAAAACAAATGGAGGATGCTAATAGATTTCAGAGAACTAAACAAGGTAACTCAAGATTT
         *       2600        *         *         *         *
   ThrGluIleGlnLeuGlyIleProHisProAlaGlyLeuAlaLysLysArgArgIleThr
CACAGAAATTCAGTTAGGAATTCCACACCCAGCAGGGTTGGCCAAGAAGAAGAATTAC
         *         *         *         *         *       2700
  ValLeuAspValGlyAspAlaTyrPheSerIleProLeuHisGluAspPheArgProTyr
TGTACTAGATGTAGGGGATGCTTACTTTTCCATACCACTACATGAGGACTTTAGACCATA
         *         *         *         *         *         *
  ThrAlaPheThrLeuProSerValAsnAsnAlaGluProGlyLysArgTyrIleTyrLys
TACTGCATTTACTCTACCATCAGTGAACAATGCAGAACCAGGAAAAAGATACATATATAA
         *         *         *       2800        *         *
   ValLeuProGlnGlyTrpLysGlySerProAlaIlePheGlnHisThrMetArgGlnVal
AGTCTTGCCACAGGGATGGAAGGGATCACCAGCAATTTTTCAACACACAATGAGACAGGT
         *         *         *         *         *         *
  LeuGluProPheArgLysAlaAsnLysAspValIleIleIleGlnTyrMetAspAspIle
ATTAGAACCATTCAGAAAAGCAAACAAGGATGTCATTATCATTCAGTACATGGATGATAT
         *       2900        *         *         *         *
   LeuIleAlaSerAspArgThrAspLeuGluHisAspArgValValLeuGlnLeuLysGlu
CTTAATAGCTAGTGACAGGACAGATTTAGAACATGATAGGGTAGTCCTGCAGCTCAAGGA
         *         *         *         *         *       3000
  LeuLeuAsnGlyLeuGlyPheSerThrProAspGluLysPheGlnLysAspProProTyr
ACTTCTAAATGGCCTAGGATTTTCTACCCCAGATGAGAAGTTCCAAAAAGACCCTCCATA
         *         *         *         *         *         *
  HisTrpMetGlyTyrGluLeuTrpProThrLysTrpLysLeuGlnLysIleGlnLeuPro
CCACTGGATGGGCTATGAACTATGGCCAACTAAATGGAAGTTGCAGAAAATACAGTTGCC
         *       3100        *         *         *         *
   GlnLysGluIleTrpThrValAsnAspIleGlnLysLeuValGlyValLeuAsnTrpAla
CCAAAAAGAAATATGGACAGTCAATGACATCCAGAAGCTAGTGGGTGTCCTAAATTGGGC
         *         *         *         *         *         *
  AlaGlnLeuTyrProGlyIleLysThrLysHisLeuCysArgLeuIleArgGlyLysMet
AGCACAACTCTACCCAGGGATAAAGACCAAACACTTATGTAGGTTAATCAGAGGAAAAAT
         *       3200        *         *         *         *
   ThrLeuThrGluGluValGlnTrpThrGluLeuAlaAlaGluLeuGluGluAsnArg
GACACTCACAGAAGAAGTACAGTGGACAGAATTACCAGAAGGAGAGCTAGAAGAAAACAG
         *         *         *         *         *       3300
  IleIleLeuSerGlnGluGlnGluGlyHisTyrTyrGlnGluGluLysGluLeuGluAla
AATTATCCTAAGCCAGGAACAAGAGGGACACTATTACCAAGAAGAAAAAGAGCTAGAAGC
         *         *         *         *         *         *
  ThrValGlnLysAspGlnGluAsnGlnTrpThrTyrLysIleHisGlnGluGluLysIle
AACAGTCCAAAAGGATCAAGAGAATCAGTGGACATATAAAATACACCAGGAAGAAAAAAT
         *         *         *       3400        *         *
   LeuLysValGluLysTyrAlaLysValLysAsnThrHisThrAsnGlyIleArgLeuLeu
TCTAAAAGTAGGAAAAATATGCAAGGTGAAAAAACACCCATACCAATGGAATCAGATTGTT
```

```
                    -continued
     *         *         *         *         *         *
  AlaGlnValValGlnLysIleGlyLysGluAlaLeuValIleTrpGlyArgIleProLys
AGCACAGGTAGTTCAGAAAATAGGAAAAGAAGCACTAGTCATTTGGGACGAATACCAAA
     *         *       3500        *         *         *
  PheHisLeuProValGluArgGluIleTrpGluGlnTrpTrpAspAsnTyrTrpGlnVal
ATTTCACCTACCAGTAGAGAGAGAAATCTGGGAGCAGTGGTGGGATAACTACTGGCAAGT
     *         *         *         *         *       3600
  ThrTrpIleProAspTrpAspPheValSerThrProProLeuValArgLeuAlaPheAsn
GACATGGATCCCAGACTGGGACTTCGTGTCTACCCCACCACTGGTCAGGTTAGCGTTTAA
     *         *         *         *         *         *
  LeuValGlyAspProIleProGlyAlaGluThrPheTyrThrAspGlySerCysAsnArg
CCTGGTAGGGGATCCTATACCAGGTGCAGAGACCTTCTACACAGATGGATCCTGCAATAG
     *         *       3700        *         *         *
  GlnSerLysGluGlyLysAslGlyTyrValThrAspArgGlyLysAspLysValLysLys
GCAATCAAAAGAAGGAAAGCAGGATATGTAACAGATAGAGGGAAAGACAAGGTAAAGAA
     *         *         *         *         *         *
  LeuGluGlnThrThrAsnGlnGlnAlaGluLeuGluAlaPheAlaMetAlaLeuThrAsp
ACTAGAGCAAACTACCAATCAGCAAGCAGAACTAGAAGCCTTTGCGATGGCACTAACAGA
     *         *       3800        *         *         *
  SerGlyProLysValAsnIleIleValAspSerGlnTyrValMetGlyIleSerAlaSer
CTCGGGTCCAAAAGTTAATATTATAGTAGACTCACAGTATGTAATGGGGATCAGTGCAAG
     *         *         *         *         *       3900
  GlnProThrGluSerGluSerLysIleValAsnGlnIleIleGluGluMetIleLysLys
CCAACCAACAGAGTCAGAAGTAAAATAGTGAACCAGATCATAGAAGAAATGATAAAAAA
     *         *         *         *         *         *
  GluAlaIleTyrValAlaTrpValProAlaHisLysGlyIleGlyGlyAsnGlnGluVal
GGAAGCAATCTATGTTGCATGGGTCCCAGCCCACAAAGGCATAGGGGGAAACCAGGAAGT
     *         *         *       4000        *         *
  AspHisLeuValSerGlnGlyIleArgGlnValLeuPheLeuGluLysIleGluProAla
AGATCATTTAGTGAGTCAGGGTATCAGACAAGTGTTGTTCCTGGAAAAAATAGAGCCCGC
     *         *         *         *         *         *
  GlnGluGluHisGluLysTyrHisSerAsnValLysGluLeuSerHisLysPheGlyIle
TCAGGAAGAACATGAAAAATATCATAGCAATGTAAAAGAACTGTCTCATAAATTTGGAAT
     *       4100        *         *         *         *
  ProAsnLeuValAlaArgGlnIleValAsnSerCysAlaGlnCysGlnGlnLysGlyGlu
ACCCAATTTAGTGGCAAGGCAAATAGTAAACTCATGTGCCCAATGTCAACAGAAAGGGGA
     *         *         *         *         *       4200
  AlaIleHisGlyGlnValAsnAlaGluLeuGlyThrTrpGlnMetAspCysThrHisLeu
AGCTATACATGGGCAAGTAAATGCAGAACTAGGGCTTGGCAAATGGACTGCACACATTT
     *         *         *         *         *         *
  GluGlyLysIleIleIleValAlaValHisValAlaSerGlyPheIleGluAlaGluVal
AGAAGGAAAGATCATTATAGTAGCAGTACATGTTGCAAGTGGATTTATAGAAGCAGAAGT
     *         *         *       4300        *         *
  IleProGlnGluSerGlyArgGlnThrAlaLeuPheLeuLeuLysLeuAlaSerArgTrp
CATCCCACAGGAATCAGGAAGACAAAGAGCACTCTTCCTATTGAAACTGGCAAGTAGGTG
     *         *         *         *         *         *
  ProIleThrHisLeuHisThrAspAsnGlyAlaAsnPheThrSerGlnGluValLysMet
GCCAATAACACACTTGCATACAGATAATGGTGCCAACTTCACTTCACAGGAGGTGAAGAT
     *       4400        *         *         *         *
  ValAlaTrpTrpIleGlyIleGluGlnSerPheGlyValProTyrAsnProGlnSerGln
GGTAGCATGGTGGATAGGTATAGAACAATCCTTTGGAGTACCTTACAATCCACAGAGCCA
     *         *         *         *         *       4500
  GlyValValGluAlaMetAsnHisHisLeuLysAsnGlnIleSerArgIleArgGluGln
AGGAGTAGTAAGCAATGAATCACCATCTAAAAAAAACCAAATAAGTAGAATCAGAGAACA
     *         *         *         *         *         *
  AlaAsnThrIleGluThrIleValLeuMetAlaIleHisCysMetAsnPheLysArgArg
GGCAAATACAATAGAAACAATAGTACTAATGGCAATTCATTGCATGAATTTTAAAAGAAG
     *         *         *         *       4600        *
  GlyGlyIleGlyAspMetThrProSerGluArgLeuIleAsnMetIleThrThrGluGln
GGGGGGAATAGGGATATGACTCCATCAGAAAGATTAATCAATATGATCACCACAGAAACA
     *         *         *         *         *         *
  GluIleGlnPheLeuGlnAlaLysAsnSerLysLeuLysAspPheArgValTyrPheArg
AGAGATACAATTCCTCCAAGCCAAAAATTCAAAATTAAAAGATTTTCGGGTATTTAACAG
     *         *       4700        *         *         *
  GluGlyArgAspGlnLeuTrpLysGlyProGlyGluLeuLeuTrplysGlyGluGlyAla
AGAAGGCAGAGATCAGTTGTGGAAAGGACCTGGGGAACTACTGTGGAAAGGAGAAGGAGC
     *         *         *         *         *       4800
  ValLeuValLysGlyThrAspIleLysIleIleIleProArgArgLysAlaLysIleIle
AGTCCTAGTCAAGGTAGGAACAGACATAAAAATAATACCAAGAAGGAAAGCCAAGATCAT
     *         *         *         *         *         *
  ArgAspTyrGlyGlyArgGlnGluMetAspSerGlySerHisLeuGluGlyAlaArgGlu
        MetGluGluAspLysArgTrpIleValValProThrTrpArgValProGlyArg
CAGACACTATGGAGGAAGACAAGAGATGGATAGTGGTTCCCACCTGGAGGGTGCCAGGGA
     *         *         *         *       4900        *
  AspGlyGluMetAla
  MetGluLysTrpHisSerLeuValLysTyrLeuLysTyrLysThrLysAspLeuGluLys
GGATGGAGAAATGGCATAGCCTTGTCAAGTATCTAAAATACAAACAAAGGATCTAGAA
     *         *         *         *         *         *
  ValCysTyrValProHisHisLysValGlyTrpAlaTrpTrpThrCysSerArgValIle
AGGTGTGCTATGTTCCCCACCATAAGGTGGGATGGGCATGGTGGACTTGCAGCAGGGTAA
```

-continued

```
              *         5000         *           *           *           *
     PheProLeuLysGlyAsnSerHisLeuGluIleGlnAlaTyrTrpAsnLeuThrProGlu
     TATTCCCATTAAAAGGAAACAGTCATCTAGAGATACAGGCATATTGGAACTTAACACCAG
              *           *         5100         *           *           *
        LysGlyTrpLeuSerSerTyrSerValArgIleThrTrpTyrThrGluLysPheTrpThr
        AAAAAGGATGGCTCTCCTCTTATTCAGTAAGAATAACTTGGTACACAGAAAAGTTCTGGA
              *           *           *           *           *           *
           AspValThrProAspCysAlaAspValLeuIleHisSerThrTyrPheProCysPheThr
           CAGATGTTACCCCAGACTGTGCAGATGTCCTAATACATAGCACTTATTTCCCTTGCTTTA
              *           *           *         5200         *           *
           AlaGlyGluValArgArgAlaIleArgGlyGluLysLeuLeuSerCysCysAspTyrPro
           CAGCAGGTGAAGTAAGAAGAGCCATCAGAGGGGAAAAGTTATTGTCCTGCTGCAATTATC
              *           *           *           *           *           *
          ArgAlaHisArgAlaGlnValProSerLeuGlnPheLeuAlaLeuValValValGlnGln
          CCCGAGCTCATAGAGCCCAGGTACCGTCACTTCAATTTCTGGCCTTAGTGGTAGTGCAAC
              *         5300         *           *           *           *
           MetThrAspProArgGluThrValProProGlyAsnSerGlyGluThrIleGly
           AsnAspArgProGlnArgAspSerThrThrArgLysGlnArgArgAsnTyrArgArg
           AAAATGACAGACCCCAGAGAGACAGTACCACCAGGAAACAGCGGGGAAGAGACTATCGGA
              *           *           *           *         5400         *
           GluAlaPheAlaTrpLeuAsnArgThrValGluAlaIleAsnArgGluAlaValAsnHis
           GlyLeuArgLeuAlaLysGlnAspSerArgSerHisLysGlnArgSerSerGluSerPro
           GAGGCCTTCGCCTGGCTAAACAGGACAGTAGAAGCCATAAACAGAGAAGCAGTGAATCAC
              *           *           *           *           *           *
          LeuProArgGluLeuIlePheGlnValTrpGlnArgSerTrpArgTyrTrpHisAspGlu
           ThrProArgThrTyrPheProGlyValAlaGluValLeuGluIleLeuAla
           CTACCCCGAGAACTTATTTTCCAGGTGTGGCAGAGGTCCTGGAGATACTGGCATGATGAA
              *           *           *         5500         *           *
          GlnGlyMetSerGluSerTyrThrLysTyrArgTyrLeuCysIleIleGlnLysAlaVal
          CAAGGGATGTCAGAAAGTTACACAAAGTATAGATATTTGTGCATAATACAGAAAGCAGTG
              *           *           *           *           *           *
          TyrMetHisValArgLysGlyCysThrCysLeuGlyArgGlyHisGlyProGlyGlyTrp
          TACATGCATGTTAGGAAAGGGTGTACTTGCCTGGGGAGGGGACATGGGCCAGGAGGTGG
              *         5600         *           *           *           *
           ArgProGlyProProProProProProProGlyLeuVal
                                                 MetAlaGluAlaProThrGlu
           AGACCAGGGCCTCCTCCTCCTCCCCCTCCAGGTCTGGTCTAATGGCTGAAGCACCAACAG
              *           *           *           *           *         5700
             LeuProProValAspGlyThrProLeuArgGluProGlyAspGluTrpIleIleGluIle
             AGCTCCCCCCCCGGTATGGGACCCCACTGAGGGAGCCAGGGGATGAGTGGATAATAGAAA
              *           *           *           *           *           *
            LeuArgGluIleLysGluGluAlaLeuLysHisPheAspProPrgLeuLeuIleAlaLeu
            TCTTGAGAGAAATAAAAGAAGAAGCTTTAAAGCATTTTGACCCTCGCTTGCTAATTGCTC
              *           *           *         5800         *           *
                         MetGluThrPreLeuLysAlaProGluSerSerLeu
             GlyLysTyrIleTyrThrArgHisGlyAspThrLeuGluGlyAlaArgGluLeuIleLys
             TTGGCAAATATATCTATACTAGACATGGAGACACCCTTGAAGGCGCCAGAGAGCTCATTA
              *           *           *           *           *           *
           LysSerCysAsnGluProPheSerArgThrSerGlnAsnAspValAlaThrGlnGluLeu
             ValLeuGlnArgAlaLeuPheThrHisPheArgAlaGlyCysGlyHisSerArgIleGly
             AAGTCCTGCAACGAGCCCTTTTCACGCACTTCAGAGCAGGATGTGGCCACTCAGAATTG
              *         5900         *           *           *           *
           AlaArgGlnGlyGluGluIleLeuSerGlnTyrArgProLeuGluThrCysAsnAsn
              GlnThrArgGlyGlyAsnProLeuSerAlaIleProThrProArgAsnMetGln
              GCCAGACAAGGGGACGAAATCCTCTCTCAGCTATACCGACCCCTAGAAACATGCAATAAC
              *           *           *           *           *         6000
           SerCysTyrCysLysArgCysCysTyrHisCysGlnMetCysPheLeuAsnLysGlyLeu
           TCATGCTATTGTAAGCCATGCTGCTACCATTGTCAGATGTGTTTTCTAAACAAGGGCTC
              *           *           *           *           *           *
           GlyIleCysTyrGluArgLysGlyArgArgArgThrProLysLysThrLysThrHis
                   MetAsnGluArgAlaAspGluGluGlyLeuGlnArgLysLeuArgLeuIle
           GGGATATGTTATGAACGAAAGGGCAGACGAAGAAGGACTCCAAAGAAAACTAAGACTCAT
              *           *           *         6100         *           *
           ProSerProThrProAspLys
           ArgLeuLeuHisGlnThr
                              MetMetAsnGlnLeuLeuIleAlaIleleuLeuAla
           CCGTCTCCTACACCAGACAAGTGAGTATGATGAATCAGCTGCTTATTGCCATTTTATTAG
              *           *           *           *           *           *
              SerAlaCysLeuValTyrCysThrGlnTyrValThrValPheTyrGlyValProThrTrp
              CTAGTGCTTGCTTAGTATATTGCACCCAATATGTAACTGTTTTCTATGGCGTACCCACGT
              *         6200         *           *           *           *
             LysAsnAlaThrThrProLeuPheCysAlaThrArgAsnArgAspThrTrpGlyThrIle
             GGAAAAATGCAACCATTCCCCTCTTTTGTGCAACCAGAAATAGGGATACTTGGGGAACCA
              *           *           *           *           *         6300
             GlnCysLeuProAspAsnAspAspTyrGlnGluIleThrLeuAsnValThrGluAlaPhe
             TACAGTGTGCCTGACAATGATGATTATCAGGAAATAACTTTGAATGTAACAGAGGCTTT
              *           *           *           *           *           *
              AspAlaTrpAsnAsnThrValThrGluGlnAlaIleGluAspValTrpHisLeuPheGlu
              TTGATGCATGGAATAATACAGTAACAGAACAAGCAATAGAGATGTCTGGCATCTATTCG
              *           *           *         6400         *           *
```

-continued

```
ThrSerIleLysProCysValLysLeuThrProLeuCysValAlaMetLysCysSerSer
AGACATCAATAAAACCATGTGTCAAACTAACACCTTTATGTGTAGCAATGAAATGCAGCA
       *         *         *         *         *         *
  ThrGluSerSerThrGlyAsnAsnThrThrSerLysSerThrSerThrThrThrThrThr
GCACAGAGAGCAGCACAGGGAACAACACAACCTCAAAGAGCACAAGCACAACCACAACCA
       *        6500       *         *         *         *
 ProThrAspGlnGluGlnGluIleSerGluAspThrProCysAlaArgAlaAspAsnCys
CACCCACAGACCAGGAGCAAGAGATAAGTGAAGGATACCCATGCGCACGCGCAGACAACT
       *         *         *         *         *        6600
    SerGlyLeuGlyGluGluGluThrIleAsnCysGlnPheAsnMetThrGlyLeuGluArg
GCTCAGGATTGGGAGAGGAAGAAACGATCAATTGCCAGTTCAATATGACAGGATTAGAAA
       *         *         *         *         *         *
   AspLysLysLysGlnTyrAsnGluThrTrpTyrSerLysAspValValCysGluThrAsn
GAGATAAGAAAAAACAGTATAATGAAACATGGTACTCAAAAGATGTGGTTTGTGAGACAA
       *         *         *        6700        *         *
   AsnSerThrAsnGlnThrGlnCysTyrMetAsnHisCysAsnThrSerValIleThrGlu
ATAATAGCACAAATCAGACCCAGTGTTACATGAACCATTGCAACACATCAGTCATCACAG
       *         *         *         *         *         *
     SerCysAspLysHisTyrTrpAspAlaIleArgPheArgTyrCysAlaProProGlyTyr
AATCATGTGACAAGCACTATTGGGATGCTATAAGGTTTAGATACTGTGCACCACCGGGTT
       *        6800       *         *         *         *
   AlaLeuLeuArgCysAsnAspThrAsnTyrSerGlyPheAlaProAsnCysSerLysVal
ATGCCCTATTAAGATGTAATGATACCAATTATTCACGCTTTGCACCCAACTGTTCTAAAG
       *         *         *         *         *        6900
   ValAlaSerThrCysThrArgMetMetGluThrGlnThrSerThrTrpPheGlyPheAsn
TAGTAGCTTCTACATGCACCAGGATGATGGAAACGCAAACTTCCACATGGTTTGGCTTTA
       *         *         *         *         *         *
  GlyThrArgAlaGluAsnArgThrTyrHisIleTyrTrpHisGlyArgAspArgThrIle
ATGGCACTAGAGCAGAGAATAGAACATATATCTATTGGCATGGCAGAGATAATAGAACTA
       *         *         *        7000        *         *
   IleSerLeuAsnLysTyrTyrAsnLeuSerLeuHisCysLysArgProGlyAsnLysThr
TCATCAGCTTAAACAAATATTATAATCTCAGTTTGCATTGTAAGAGGCCAGGGAATAAGA
       *         *         *         *         *         *
   ValLysGlnIleMetLeuMetSerGlyHisValPheHisSerHisTyrGlnProIleAsn
CAGTGAAACAAATAATGCTTATGTCAGGACATGTGTTTCACTCCCACTACCAGCCGATCA
       *        7100       *         *         *         *
   LysArgProArgGlnAlaTrpCysTrpPheLysGlyLysTrpLysAspAlaMetGlnGlu
ATAAAAGACCCAGACAAGCATGGTGCTGGTTCAAAGGCAAATGGAAAGACGCCATGCAGG
       *         *         *         *         *        7200
  ValLysGluThrLeuAlaLysHisProArgTyrArgGlyThrAsnAspThrArgAsnIle
AGGTGAAGGAAACCCTTGCAAAACATCCCAGGTATAGAGGAACCAATGCACAAGGAATA
       *         *         *         *         *         *
   SerPheAlaAlaProGlyLysGlySerAspProGluValAlaTyrMetTrpThrAsnCys
TTAGCTTTGCAGCGCCAGGAAAAGGCTCAGACCCAGAAGTAGCATACATGTGGACTAACT
       *         *         *        7300        *         *
   ArgGlyGluPheLeuTyrCysAsnMetThrTrpPheLeuAsnTrpIleGluAsnLysThr
GCAGAGGAGAGTTTCTCTACTGGAACATGACTTGGTTCCTCAATTGGATAGAGAATAAGA
       *         *         *         *         *         *
   HisArgAsnTyrAlaProCysHisIleLysGlnIleIleAsnThrTrpHisLysValGly
CACACCCCAATTATGCACCGTGCCATATAAAGCAAATAATTAACACATGGCATAAGGTAG
       *        7400       *         *         *         *
   ArgAsnValTyrLeuProProArgGluGlyGluLeuSerCysAsnSerThrValThrSer
GGAGAAATGTATATTTGCCTCCCAGGGAAGGGGAGCTGTCCTGCAACTCAACAGTAACCA
       *         *         *         *         *        7500
   IleIleAlaAsnIleAspTrpGlnAsnAsnAsnGlnThrAsnIleThrPheSerAlaGlu
GCATAATTGCTAACATTGACTGGCAAAACAATAATCAGACAAACATTACCTTTAGTGCAG
       *         *         *         *         *         *
   ValAlaGluLeuTyrArgLeuGluLeuGlyAspTyrLysLeuValGluIleThrProIle
AGGTGGCAGAACTATACAGATTGGAGTTGGGAGATTATAAATTGGTAGAAATAACACCAA
       *         *         *        7600        *         *
   GlyPheAlaProThrLysGluLysArgTyrSerSerAlaHisGlyArgHisThrArgGly
TTGGCTTCGCACCTACAAAAGAAAAAAGATACTCCTCTGCTCACGGGAGACATACAAGAG
       *         *         *         *         *         *
   ValPheValLeuGlyPheLeuGlyPheLeuAlaThrAlaGlySerAlaMetGlyAlaAla
GTGTTCGTGCTAGGGTTCTTGGGTTTTCTCGCAACAGCAGGTTCTGCAATGGGCGCGG
       *        7700       *         *         *         *
   SerLeuThrValSerAlaGlnSerArgThrLeuLeuAlaGlyIleValGlnGlnGlnGln
CGTCCCTGACCGTGTCGGCTCAGTCCCGGACTTTACTGGCCGGGATAGTGCAGCAACAGC
       *         *         *         *         *        7800
   GlnLeuLeuAspValValLysArgGlnGlnGluLeuLeuArgLeuThrValTrpGlyThr
AACAGCTGTTGGACGTGGTCAAGAGACAACAAGAACTGTTGCGACTGACCGTCTGGGGAA
       *         *         *         *         *         *
   LysAsnLeuGlnAlaArgValThrAlaIleGluLysTyrLeuGlnAspGlnAlaArgLeu
CGAAAAACCTCCAGGCAACAGTCACTGCTATAGAGAAGTACCTACAGGACCAGGCGCGGC
       *         *         *        7900        *         *
  AsnSerTrpGlyCysAlaPheArgGlnValCysHisThrThrValProTrpValAsnAsp
TAAATTCATGGGGATGTGCGTTTAGACAAGTCTGCCACACTACTGTACCATGGGTTAATG
       *         *         *         *         *         *
    SerLeuAlaProAspTrpAspAsnMetThrTrpGlnGluTrpGluLysGlnValArgTyr
ATTCCTTAGCACCTGACTGGGACAATATGACGTGGCAGGAATGGGAAAAACAAGTCCGCT
```

```
                              *         8000         *         *         *         *
      LeuGluAlaAsnIleSerLysSerLeuGluGlnAlaGlnIleGlnGlnGluLysAsnMet
      ACCTGGAGGCAAATATCAGTAAAAGTTTAGAACAGGCACAAATTCAGCAAGAGAAAAATA
             *         *         *         *        8100
        TyrGluLeuGlnLysLeuAsnSerTrpAspIlePheGlyAsnTrpPheAspLeuThrSer
      TGTATGAACTACAAAAATTAAATAGCTGGGATATTTTTGGCAATTGGTTTGACTTAACCT
             *         *         *         *         *         *
         TyrValLysTyrIleGlnTyrGlyValLeuIleIleValAlaValIleAlaLeuArgIle
      CCTGGGTCAAGTATATTCAATATGGAGTGCTTATAATAGTAGCAGTAATAGCTTTAAGAA
             *         *         *        8200         *         *
         ValIleTyrValValGlnMetLeuSerArgLeuArgLysGlyTyrArgProValPheSer
      TAGTGATATATGTAGTACAAATGTTAAGTAGGCTTAGAAAGGGCTATAGGCCTGTTTTCT
             *         *         *         *         *         *
                                 SerIleSerThrArgThrGlyAspSerGlnPro
                              AsnProTyrProGlnGlyProGlyThrAlaSerGln
         SerProProGlyTyrIleGlnGlnIleHisIleHisLysAspArgGlyGlnProAlaAsn
      CTTCCCCCCCCGGTTATATCCAACAGATCCATATCCACAAGGACCGGGGACAGCCAGCCA
                       *        8300         *         *         *
      ThrLysLysGlnLysLysThrValGluAlaThrValGluThrAspThrGlyProGlyArg
         ArgArgArgAsnArgArgArgTrpLysGlnArgTrpArgGlnIleLeuAlaLeuAlaAsp
          GluGlyThrGluGluAspGlyGlySerAsnGlyGlyAspArgTyrTrpProTrpProIle
      ACGAAGAAACAGAAGAAGACGGTCGAAGCAACGGTGGAGACAGATACTGGCCCTGGCCGA
             *         *         *         *         *        8400
         SerIleTyrThrPheProAspProProAlaAspSerProLeuAspGlnThrIleGlnHis
          AlaTyrIleHisPheLeuIleArgGlnLeuIleArgLeuLeuThrArgLeuTyrSerIle
      TAGCATATATACATTTCCTGATCCGCCAGCTGATTCGCCTCTTGACCAGACTATACAGCA
             *         *         *         *         *         *
         LeuGlnGlyLeuThrIleGlnGluLeuProAspProProThrHisLeuProGluSerGln
          CysArgAspLeuLeuSerArgSerPheLeuThrLeuGlnLeuIleTyrGlnAsnLeuArg
      TCTGCAGGGACTTACTATCCAGGAGCTTCCTGACCCTCCAACTCATCTACCAGAATCTCA
             *         *         *        8500         *         *
         ArgLeuALAGluThr                      MetGlyAlaSerGlySerLysLys
         AspTrpLeuArgLeuArgThrAlaPheLeuGlnTyrGlyCysGlyTrpIleGlnGluAla
      GAGACTGGCTGAGACTTAGAACAGCCTTCTTCCAATATGGGTGCGAGTGGATCCAAGAAG
             *         *         *         *         *         *
      HisSerArgProProArgGlyLeuGlnGluArgLeuLeuArgAlaArgAlaGlyAlaCys
        PheGlnAlaAlaAlaArgAlaThrArgGluThrLeuAlaGlyAlaCysArgGlyLeuTrp
      CATTCCAGGCCGCCGCGAGGGCTACAAGAGAGACTCTTGCGGGCGCGTGCAGGGGCTTCT
                       *        8600         *         *         *
      GlyGlyTyrTrpAsnGluSerGlyGlyGluTyrSerArgPheGlnGluGlySerAspArg
         ArgValLeuGluArgIleGlyArgGlyIleLeuAlaValProArgArgIleArgGlnGly
      GCAGGGTATTGGAACGAATCGGGAGGGGAATACTCGCGGTTCCAAGAAGGATCAGACAGG
             *         *         *         *         *        8700
      GluGlnLysSerProSerCysGluGlyArgGlnTyrGlnGlnGlyAspPheMetAsnThr
          AlaGluIleAlaLeuLeu
      GAGCAGAAATCGCCCTCCTGTGAGGGACGGCAGTATCAGCAGGGAGACTTTATGAATACT
             *         *         *         *         *         *
      ProTrpLysAspProAlaAlaGluArgGluLysAsnLeuTyrArgGlnGlnAsnMetAsp
      CCATGGAAGGACCCAGCAGCAGAAAGGGAGAAAAATTTGTACAGGCAACAAAATATGGAT
                       *        8800         *         *         *
      AspValAspSerAspAspAspAspGlnValArgValSerValThrProLysValProLeu
      GATGTAGATTCAGATGATGATGACCAAGTAAGAGTTTCTGTCACACCAAAAGTACCACTA
             *         *         *         *         *         *
      ArgProMetThrHisArgLeuAlaIleAspMetSerHisLeuIleLysThrArgGlyGly
      AGACCAATGACACATACATTGGCAATAGATATGTCACATTTAATAAAAACAAGGGGGGA
                       *        8900         *         *         *
      LeuGluGlyMetPheTyrSerGluArgArgHisLysIleLeuAsnIleTyrLeuGluLys
      CTGGAAGGGATGTTTTACAGTGAAAGAAGACATAAAATCTTAAATATATACTTAGAAAAG
             *         *         *         *         *        9000
      GluGluGlyIleIleAlaAspTrpGLnAsnTyrThrHisGlyProGlyValArgTyrPro
      GAAGAAGGGATAATTGCAGATTGGCAGAACTACACTCATGGGCCAGGAGTAAGATACCCA
             *         *         *         *         *         *
      MetPhePheGlyTrpLeuTrpLysLeuValProValAspValProGlnGluGlyGluAsp
      ATGTTCTTTGGGTGGCTATGGAAGCTAGTACCAGTAGATGTCCCACAAGAAGGGGAGGAC
             *         *         *        9100         *         *
      ThrGluThrHisCysLeuValHisProAlaGlnThrSerLysPheAspAspProHisGly
      ACTGAGACTCACTGCTTAGTACATCCAGCACAAACAAGCAAGTTTGATGACCCGCATGGG
             *         *         *         *         *         *
      GluThrLeuValTrpGluPheAspProLeuLeuAlaTyrSerTyrGluAlaPheIleArg
      GAGACACTAGTCTGGGAGTTTGATCCCTTGCTGGCTTATAGTTACGAGGCTTTTATTCGG
                      9200         *         *         *         *
      TyrProGluGluPheGlyHisLysSerGlyLeuProGluGluGluTrpLysAlaArgLeu
      TACCCAGAGGAATTTGGGCACAAGTCAGGCCTGCCAGAGGAAGAGTGGAAGGCGAGACTG
             *         *         *         *         *        9300
      LysAlaArgGlyIleProPheSer
      AAAGCAAGAGGAATACCATTTAGTTAAAGACAGGAACAGCTATACTTGGTCAGGGCAGGA
             *         *         *         *         *         *
      AGTAACTAACAGAAACAGCTGAGACTGCAGGGACTTTCCAGAAGGGGCTGTAACCAAGGG
             *         *         *         *        9400
      AGGGACATGGGAGGAGCTGGTGGGAACGCCCTCATATTCTCTGTATAAATATACCCGCT
```

-continued

```
AGCTTGCATTGTACTTCCGTCGCTCTGCGGAGAGGCTGGCAGATTGAGCCCTGGGAGGTT
     *         *         *         *         *         *
               9500      *         *         *         *
CTCTCCAGCAGTAGCAGGTAGAGCCTGGGTGTTCCCTGCTAGACTCTCACCAGCACTTGG
     *         *         *         *         *       9600
CCGGTGCTGGGCAGACGGCCCCACGCTTGCTTGCTTAAAAACCTCCTTAATAAAGCTGCC
     *         *         *         *         *         *
AGTTAGAAGCA
     *
```

Example 5

Sequences of the Coding Regions for the Envelope Protein and GAG Product of the ROD HIV-2 Isolate Through experimental analysis of the HIV-2 ROD isolate, the following sequences were identified for the regions encoding the env and gag gene products. One of ordinary skill in the art will recognize that the numbering for both gene regions which follow begins for convenience with "1" rather than the corresponding number for its initial nucleotide as given in Example 4, above, in the context of the complete genomic sequence.

```
Envelopesequence
MetMetAsnGlnLeuLeuIleAlaIleLeuLeuAlaSerAlaCys
ATGATGAATCAGCTGCTTATTGCCATTTTATTAGCTAGTGCTTGC
     *         *         *         *         *

LeuValTyrCysThrGlnTyrValThrValPheTyrGlyValPro
TTAGTATATTGCAGCCAATATGTAACTGTTTTCTATGGCGTACCC
     *         *         *         *         *

ThrTrpLysAsnAlaThrIleProLeuPheCysAlaThrArgAsn
ACGTGGAAAAATGCAACCATTCCCCTGTTTTGTGCAACCAGAAAT
              100        *         *         *

ArgAspThrTrpGlyThrIleGlaCysLeuProAspAspAspAsp
AGGGATACTTGGGGAACCATACAGTGGTTGCCTGACAATGATGAT
     *         *         *         *         *

TyrGlnGluIleThrLeuAsnValThrGluAlaPheAspAlaTrp
TATCAGGAAATAACTTTTGAATGTAACAGAGGCTTTTGATGCATGG
     *         *        200        *         *

AsnAsnThrValThrGluGlnAlaIleGluAspValTrpHisLeu
AATAATACAGTAACAGAACAAGCAATAGAAGATGTCTGGCATCTA
     *         *         *         *         *

PheGluThrSerIleLysProCysValLysLeuThrProLeuCys
TTCGAGACATCAATAAAACCATGTGTCAAACTAACACCTTTATGT
     *         *         *        300        *

ValAlaMetLysCysSerSerThrGluSerSerThrGlyAsnAsn
GTAGCAATGAAATGCAGCAGCACAGAGAGCAGCACAGGGAACAAG
     *         *         *         *         *

ThrThrSerLysSerThrSerThrThrThrThrThrProThrAsp
ACAACCTCAAAGAGCACAAGCACAACCACAACCACACCCAGAGAC
     *         *         *        400

GlnGluGlnGluIleSerGluAspThrProCysAlaArgAlaAsp
CAGGAGCAAGAGATAAGTGAGGATACTCCATGCGCACGCGCAGAC
     *         *         *         *         *

AsnCysSerGlyLeuGlyGluGluGluThrIleAsnCysGlnPhe
AACTGCTCAGGATTGGGAGAGGAAGAAACGATCAATTGCCAGTTC
     *         *         *         *         *

AsnMetThrGlyLeuGluArgAspLysLysLysGlnTyrAsnGlu
AATATGACAGGATTAGAAAGAGATAAGAAAAAACAGTATAATGAA
    500        *         *         *         *
```

-continued
```
ThrTrpTyrSerLysAspValValCysGluThrAsnAsnSerThr
ACATGGTACTCAAAAGATGTGGTTTGTGAGACAAATAATAGCACA
     *         *         *         *

AsnGlnThrGlnCysTyrMetAsnHisCysAsnThrSerValIle
AATCAGACCCAGTGTTACATGAACCATTGCAACACATCAGTCATC
     *        600        *         *         *

ThrGluSerCysAspLysHisTyrTrpAspAlaIleArgPheArg
ACAGAATCATGTGACAAGCACTATTGGGATGCTATAAGGTTTAGA
     *         *         *         *

TyrCysAlaProProGlyTyrAlaLeuLeuArgCysAsnAspThr
TACTGTGCACCACCGGGTTATGCCCTATTAAGATGTAATGATACC
     *         *        700        *         *

AsnTyrSerGlyPheAlaProAsnCysSerLysValValAlaSer
AATTATTCAGGCTTTGCACCCAACTGTTCTAAAGTAGTAGCTTCT
     *         *         *         *

ThrCysThrArgMetMetGluThrGlnThrSerThrTrpPheGly
ACATGCACCAGGATGATGGAAACGCAAACTTCCACATGGTTTGGC
     *         *         *        800        *

PheAsnGlyThrArgAlaGluAsnArgThrTyrIleTyrTrpHis
TTTAATGGCACTAGAGCAGAGAATAGAACATATATCTATTGGCAT
     *         *         *         *

GlyArgAspAsnArgThrIleIleSerLeuAsnLysTyrTyrAsn
GGCAGAGATAATAGAACTATCATCAGCTTAAACAAATATTATAAT
     *         *         *         *        900

LeuSerLeuHisCysLysArgProGlyAsnLysThrValLysGla
CTCAGTTTGCATTGTAAGAGGCCAGGGAATAAGACAGTGAAACAA
     *         *         *         *

IleMetLeuMetSerGlyHisValPheHisSerHisTyrGlnPro
ATAATGCTTATGTCAGGACATGTGTTTCACTCCCACTACCAGCCG
     *         *         *         *         *

IleAsnLysArgProArgGlnAlaTrpCysTrpPheLysGlyLys
ATCAATAAAAGACCCAGACAAGCATGGTGCTGGTTCAAAGGCAAA
    1000        *         *         *

TrpLysAspAlaMetGlnGluValLysThrLeuAlaLysHisPro
TGGAAAGACGCCATGCAGGAGGTGAAGACCCTTGCAAAACATCCC
     *         *         *         *         *

ArgTyrArgGlyThrAsnAspThrArgAsnIleSerPheAlaAla
AGGTATAGAGGAACCAATGACACAAGGAATATTAGCTTTGCAGCG
     *        1100        *         *

ProGlyLysGlySerAspProGluValAlaTyrMetTrpThrAsn
CCAGGAAAAGGCTCAGACCCAGAAGTAGCATACATGTGGACTAAC
     *         *         *         *         *

CysArgGlyGluPheLeuTyrCysAsnMetThrTrpPheLeuAsn
TGCAGAGGAGAGTTTCTCTACTGCAACATGACTTGGTTCCTCAAT
     *         *        1200        *

TrpIleGluAsnLysThrHisArgAsnTyrAlaProCysHisIle
TGGATAGAGAATAAGACACACCGCAATTATGCACCGTGCCATATA
     *         *         *         *         *

LysGlnIleIleAsnThrTrpHisLysValGlyArgAsnValTyr
AAGCAAATAATTAACACATGGCATAAGGTAGGGAGAAATGTATAT
```

-continued

```
LeuProProArgGluGlyGluLeuSerCysAsnSerThrValThr
TTGCCTCCCAGGGAAGGGGAGCTGTCCTGCAACTCAACAGTAACC
    *         *         *         *         *

SerIleIleAlaAsnIleAspTrpGlnAsnAsnAsnGlnThrAsn
AGCATAATTGCTAACATTGACTGGCAAAACAATAATCAGACAAAC
    *         *         *         *         *

IleThrPheSerAlaGluValAlaGluLeuTyrArgLeuGluLeu
ATTACCTTTAGTGCAGAGGTGGCAGAACTATACAGATTGGAGTTG
1400        *         *         *         *

GlyAspTyrLysLeuValGluIleThrProIleGlyPheAlaPro
GGAGATTATAAATTGGTAGAAATAACACCAATTGGCTTCGCACCT
    *         *         *         *         *

ThrLysGluLysArgTyrSerSerAlaHisGlyArgHisThrArg
ACAAAAGAAAAAAGATACTCCTCTGCTGACGGGAGACATACAAGA
    *       1500        *         *         *

GlyValPheValLeuGlyPheLeuGlyPheLeuAlaThrAlaGly
GGTGTGTTCGTGCTAGGGTTCTTGGGTTTTCTCGCAACAGCAGGT
    *         *         *         *         *

SerAlaMetGlyAlaArgAlaSerLeuThrValSerAlaGlaSer
TCTGCAATGGGCGCTCGAGCGTCCCTGACCGTGTCGGCTCAGTCC
    *         *       1600        *         *

ArgThrLeuLeuAlaGlyIleValGlnGlnGlnGlnGlnLeuLeu
CGGACTTTACTGGCCGGGATAGTGCAGCAACAGCAACAGCTCTTC
    *         *         *         *         *

AspValValLysArgGlnGlnGluLeuLeuArgLeuThrValTrp
GACGTGGTCAAGAGACAACAAGAACTGTTGCGACTGACCGTCTGG
    *         *         *       1700        *

GlyThrLysAsnLeuGlnAlaArgValThrAlaIleGluLysTyr
GGAACGAAAAACCTCCAGGCAAGAGTCACTGCTATAGAAGTAG
    *         *         *         *         *

LeuGlnAspGlnAlaArgLeuAsnSerTrpGlyCysAlaPheArg
CTACAGGACCAGGCGCGGCTAAATTCATGGGGATGTGCGTTTAGA
    *         *         *         *       1800

GlnValCysHisThrThrValProTrpValAsnAspSerLeuAla
CAAGTCTGCCACACTACTGTACCATGGGTTAATGATTCCTTAGCA
    *         *         *         *         *

ProAspTrpAspAsnMetThrTrpGluGluTrpGluLysGlaVal
CCTGACTGGGACAATATGACGTGGCAGGAATGGGAAAAACAAGTC
    *         *         *         *         *

ArgTyrLeuGluAlaAsnIleSerLysSerLeuGluGlnAlaGln
CGCTACCTGGAGGCAAATATCAGTAAAAGTTTAGAACAGGCACAA
  1900        *         *         *         *

IleGlnGlnGluLysAsnMetTyrGluLeuGlnLysLeuAsnSer
ATTCAGCAAGAGAAAAATATGTATGAACTACAAAAATTAAATAGC
    *         *         *         *         *

TrpAspIlePheGlyAsnTrpPheAspLeuThrSerTrpValLys
TGGGATATTTTTGGCAATTGGTTTGACTTAACCTCCTGGGTCAAG
    *         *       2000        *         *

TyrIleGlnTyrGlyValLeuIleIleValAlaValIleAlaLeu
TATATTCAATATGGAGTGCTTATAATAGTAGCAGTAATAGCTTTA
    *         *         *         *         *

ArgIleValIleTyrValValGlnMetLeuSerArgLeuArgLys
AGAATAGTGATATATGTAGTACAAATGTTAAGTAGGCTTAGAAAG
    *         *         *       2100        *

GlyTyrArgProValPheSerSerProProGlyTyrIleGla***
GGCTATAGGCCTGTTTTCTCTTCCCCCCCCGGTTATATCCAATAG
    *         *         *         *         *

IleHisIleHisLysAspArgGlyGlnProAlaAsnGluGluThr
ATCCATATCCACAAGGACCGGGGACAGCCAGCCAACGAAGAAACA
```

```
GluGluAspGlyGlySerAsnGlyGlyAspArgTyrTrpProTrp
GAAGAAGACGGTGGAAGCAACGGTGGAGACAGATACTGGCCCTGG
    *         *         *         *         *

ProIleAlaTyrIleHisPheLeuIleArgGlnLeuIleArgLeu
GCGATAGCATATATACATTTCCTGATCCGCCAGCTGATTCGCCTC
    *         *         *         *         *

LeuThrArgLeuTyrSerIleCysArgAspLeuLeuSerArgSer
TTGACCAGACTATACAGCATCTGCAGGGACTTACTATCCAGGAGC
  2300        *         *         *         *

PheLeuThrLeuGlnLeuIleTyrGlaAsnLeuArgAspTyrLeu
TTCCTGACCCTCCAACTCATCTACCAGAATCTCAGAGACTGGCTG
    *         *         *         *         *

ArgLeuArgThrAlaPheLeuGlnTyrGlyCysGluTrpIleGla
AGACTTAGAACAGCCTTCTTGCAATATGGGTGCGAGTGGATCCAA
    *       2400        *         *         *

GluAlaPheGlnAlaAlaAlaArgAlaThrArgGluThrLeuAla
GAAGCATTCCAGGCCGCCGCGAGGGCTACAAGAGAGACTCTTGCG
    *         *         *         *         *

GlyAlaCysArgGlyLeuTrpArgValLeuGluArgIleGlyArg
GGCGCGTGCAGGGGCTTGTGGAGGGTATTGGAACGAATCGGGAGG
    *         *       2500        *         *

GlyIleLeuAlaValProArgArgIleArgGlnGlyAlaGluIle
GGAATACTCGCGGTTCCAAGAAGGATCAGACAGGGAGCAGAAATC
    *         *         *         *         *

AlaLeuLeu***GlyThrAlaValSerAlaGlyArgLeuTyrGlu
GCCCTCCTGTGAGGGACGGCAGTATCAGCAGGGAGACTTTATGAA
    *         *         *       2600        *

TyrSerMetGluGlyProSerSerArgLysGlyGluLysPheVal
TACTCCATGGAAGGACCCAGCAGCAGAAAGGGAGAAAAATTTGTA
    *         *         *         *         *

GlnAlaThrLysTyrGly
CAGGCAACAAAATATGGA
    *         *

Gagsequence
MetGlyAlaArgAsnSerValLeuArgGlyLysLysAlaAspGlu
ATGGGCGCGAGAAACTCCGTCTTGAGAGGGAAAAAAGCAGCTGAA
    *         *         *         *         *

LeuGluArgIleArgLeuArgProGlyGlyLysLysLysTyrArg
TTAGAAAGAATCAGGTTACGGCCCGGCGGAAAGAAAAAGTACAGG
    *         *         *         *         *

LeuLysHisIleValTrpAlaAlaAsnLysLeuAspArgPheGly
CTAAAACATATTGTGTGGGCAGCGAATAAATTGCACAGATTCGGA
  100         *         *         *         *

LeuAlaGluSerLeuLeuGluSerLysGluGlyCysGlnLysIle
TTAGCAGAGAGCCTGTTGGAGTCAAAAGAGGGTTGTCAAAAAATT
    *         *         *         *         *

LeuThrValLeuAspProMetValProThrGlySerGluAsnLeu
CTTACAGTTTTAGATCCAATGGTACCGACAGGTTCAGAAAATTTA
    *         *         *       200         *

LysSerLeuPheAsnThrValCysValIleTrpCysIleHisAla
AAAAGTCTTTTTAATACTGTCTGCGTCATTTGGTGCATACACGCA
    *         *         *         *         *

GluGluLysValLysAspThrGluGlyAlaLysGlnIleValArg
GAAGAGAAAGTGAAAGATACTGAAGGAGCAAAACAAATAGTGCGG
    *         *       300         *         *

ArgHisLeuValAlaGluThrGlyThrAlaGluLysMetProSer
AGACATCTAGTGGCAGAAACAGGAACTGCAGAGAAAATGCCAAGC
    *         *         *         *         *

ThrSerArgProThrAlaProSerSerGluLysGlyGlyAsnTyr
```

-continued
```
ACAAGTAGACCAACAGCACCATCTAGCGAGAAGGGAGGAAATTAC
    *         *         *         *        400

ProValGlnHisValGlyGlyAsnTyrThrHisIleProLeuSer
CCAGTGCAACATGTAGGCGGCAACTACACCCATATACCGCTGAGT
    *         *         *         *         *

ProArgThrLeuAsnAlaTrpValLysLeuValGluGluLysLys
CCCCGAACCCTAAATGCCTGGGTAAAATTAGTAGAGGAAAAAAAG
    *         *         *         *         *

PheGlyAlaGluValValProGlyPheGlnAlaLeuSerGluGly
TTCGGGGCAGAAGTAGTGCCAGGATTTCAGGCACTCTCAGAAGGC
   500        *         *         *         *

CysThrProTyrAspIleAsnGlnMetLeuAsnCysValGlyAsp
TGCACGCCCTATGATATCAACCAAATGCTTAATTGTGTGGGCGAC
    *         *         *         *         *

HisGlnAlaAlaMetGlnIleIleArgGluIleIleAsnGluGlu
CATCAAGCAGCCATGCAGATAATCAGGGAGATTATCAATGAGGAA
    *        600        *         *         *

AlaAlaGluTrpAspValGlnHisProIleProGlyProLeuPro
GCAGCAGAATGGGATGTGCAACATCCAATACCAGGCCCCTTACCA
    *         *         *         *         *

AlaGlyGlnLeuArgGluProArgGlySerAspIleAlaGlyThr
GCGGGGCAGCTTAGAGAGCCAAGGGGATCTGACATAGCAGGGAGA
    *         *        700        *         *

ThrSerThrValGluGluGlnIleGlnTrpMetPreArgProGln
ACAAGCACAGTAGAAGAACAGATCCAGTGGATGTTTAGGCCACAA
    *         *         *         *         *

AsnProValProValGlyAsnIleTyrArgArgTrpIleGlnIle
AATCCTGTACCAGTAGGAAACATCTATAGAAGATGGATCCAGATA
    *         *         *        800        *

GlyLeuGlnLysCysValArgMetTyrAsnProThrAsnIleLeu
GGATTGCAGAAGTGTGTCAGGATGTACAACCCGACCAACATCCTA
    *         *         *         *         *

AspIleLysGlnGlyProLysGluProPheGlnSerTyrValAsp
GACATAAAACAGGGACCAAAGGAGCCGTTCCAAAGCTATGTAGAT
    *         *         *         *        900

ArgPheTyrLysSerLeuArgAlaGluGlnThrAspProAlaVal
AGATTCTACAAAAGCTTGAGGGCAGAACAAACAGATCCAGCAGTG
    *         *         *         *         *

LysAsnTrpMetThrGlnThrLeuLeuValGlnAsnAlaAsnPro
AAGAATTGGATGACCCAAACACTGCTAGTACAAAATGCCAACCCA
    *         *         *         *         *

AspCysLysLeuValLeuLysGlyLeuGlyMetAsnProThrLeu
GACTGTAAATTAGTGCTAAAAGGACTAGGGATGAACCCTACCTTA
   1000        *         *         *         *

GluGluMetLeuThrAlaCysGlnGlyValGlyGlyProGlyGln
GAAGAGATGCTGACCGCCTGTCAGGGCGTAGGTGGGCCAGGCCAG
    *         *         *         *         *

LysAlaArgLeuMetAlaGluAlaLeuLysGluValIleGlyPro
AAAGCTAGATTAATGGCAGAGGCCCTGAAAGAGGTCATAGGACCT
    *        1100        *         *         *

AlaProIleProPheAlaAlaAlaGlnGlnArgLysAlaPheLys
GCCCCTATCCCATTCGCAGCAGCCCAGCAGAGAAAGGCATTTAAA
    *         *         *         *         *

CysTrpAsnCysGlyLysGluGlyHisSerAlaArgGlnCysArg
TGCTGGAACTGTGGAAAGGAAGGGCACTCGGCAAGACAATGCCGA
    *         *        1200        *         *

AlaProArgArgGlnGlyCysTrpLysCysGlyLysProGlyHis
GCACCTAGAAGGCAGGGCTGCTGGAAGTGTGGTAAGCCAGGACAC
    *         *         *         *         *

IleMetThrAsnCysProAspArgGlnAlaGlyPheLeuGlyLeu
ATCATGACAAACTGCCCAGATAGACAGGCAGGTTTTTTAGGACTG
```
-continued
```
    *         *         *        1300

ProGlnGlyLeuThrProThrAlaProProValAspProAlaVal
GGCCCTTGGGGAAAGAAGCCCCGCAACTTCCCCGTGGCCCAAGTT
    *         *         *         *         *

ProGlnGlyLeuThrProThrAlaProProValAspProAlaVal
CCGCAGGGGCTGACACCAACAGCACCCCGAGTGGATCCAGCAGTG
    *         *         *         *         *

AspLeuLeuGluLysTyrMetGlnGlnGlyLysArgGlnArgGlu
GATCTACTGGAGAAATATATGCAGCAAGGGAAAAGACAGAGAGAG
   1400        *         *         *         *

GlnArgGluArgProTyrLysGluValThrGluAspLeuLeuHis
CAGAGAGAGGACCATACAAGGAAGTGACAGAGGACTTACTGCAC
    *         *         *         *         *

LeuGluGlnGlyGluThrProTyrArgGluProProThrGluAsp
CTCGAGCAGGGGGAGACACCATACAGGGAGCCACCAACAGAGGAC
    *        1500        *         *         *

LeuLeuHisLeuAsnSerLeuPheGlyLysAspGln
TTGCTGCACCTCAATTCTCTCTTTGGAAAAGACCAG
    *         *         *
```

Example 6

Peptide Sequences Encoded By The ENV and GAG genes

The following coding regions for antigenic peptides, identified for convenience only by the nucleotide numbers of Example 5, within the env and gag gene regions are of particular interest.

```
env1 (1732-1809)
                        ArgValThrAlaIleGluLysTyr
                        AGAGTCACTGCTATAGAGAAGTAG
                            *         *
LeuGluAspGlnAlaArgLeuAsnSerTrpGlyCysAlaPheArg
CTACAGGACCAGGCGCGGCTAAATTCATGGGGATGTGCGTTTAGA

*         *         *         *        1000
GlnValCys
CAAGTCTGC env2 (1912-1983)
                         SerLysSerLeuGluGlnAlaGln
                         AGTAAAAGTTTAGAACAGGCACAA
                                              **
IleGlnGlnGluLysAsnMetTyrGluLeuGlnLysLeuAsnSer
ATTCAGCAAGAGAAAATATGTATGAACTACAAAAATTAAATACC
   1940        *         *         *         *

Trp
TGG env3 (1482-1530)
ProThrLysGluLysArgTyrSerSerAlaHisGlyArgHisThrArg
CCTACAAAAGAAAAAAGATCATCCTCTGCTCACGGGAGACATACAAGA
    *        1500        *         *         * env4 (55-129)
            CysThrGlnTyrValThrValPheTyrGlyValPro
            TGCACCCAATATGTAACTGTTTTCTATGGCGTACCC
                *         *         *         *

ThrTrpLysAsnAlaThrIleProLeuPheCysAlaThr
ACGTGGAAAAATGCAACCATTCCCCTGTTTTGTGCAACC
   100        *         *         * env5 (175-231)
                                      AspAsp
```

-continued

```
                                         GATGAT
                                              *

TyrGluGluIleThrLeuAsnValThrGluAlaPheAspAlaTrp
TATCAGGAAATAACTTTGAATGTAACAGAGGCTTTTGATGCATGG
             *        200        *        *

AsnAsn
AATAAT env6 (274-330)
    GluThrSerIleLysProCysValLysLeuThrProLeuCys
GACACATCAATAAAACCATGTGTGAAACTAACACCTTTATGT
        *        *        300        *

ValAlaMetLysCys
GTAGCAATGAAATGC
        *        * env7 (607-660)
                        AsnHisCysAsnThrSerValIle
                        AACCATTGCAACACATCAGTCATC
                           610      *         *

ThrGluSerCysAspLysHisTyrTrpAsp
ACAGAATCATGTGACAAGCACTATTGGGAT
        *        *         * env8 (661-720)
                              AlaIleArgPheArg
                              GCTATAAGGTTTAGA
                                           *

TyrCysAlaProProGlyTyrAlaLeuLeuArgCysAsnAspThr
TACTGTGCACCACCGGGTTATGCCCTATTAAGATGTAATGATACC
        *         *        700        *        * env9 (997-1044)
       LysArgProArgGlnAlaTrpCysTrpPheLysGlyLys
       AAAAGACCCAGACAAGCATGGTGCTGGTTCAAAGGCAAA
           1000        *        *         *

TrpLysAsp
TGGAAAGAC env10 (1132-1215)
       LysGlySerAspProGluValAlaTyrMetTrpThrAsn
       AAAGGCTCAGACCCAGAAGTAGCATACATGTGGACTAAC
          *         *         *         *
```

-continued
```
       CysArgGlyGluPheLeuTyrCysAsnMetThrTrpPheLeuAsn
       TGCAGAGGAGAGTTTCTCTACTGCAACATGACTTGGTTCCTCAAT
           *           *         1200         * env11 (1237-1305)
                          ArgAsnTyrAlaProCysHisIle
                          CGCAATTATGCACCGTGCCATATA
                                              *

LysGlnIleIleAsnThrTrpHisLysValGlyArgAsnValTyr
    AAGCAAATAATTAACACATGGCATAAGGTAGGGAGAAATGTATAT
        *         *         *          1300 gag1 (991-1053)
AspCysLysLeuValLeuLysGlyLeuGlyMetAsnProThrLeu
GACTGTAAATTAGTGCTAAAAGGACTAGGGATGAACCCTACCTTA
           1000       *        *         *
GluGluMetLeuThrAla
GAAGAGATGCTGACCGCC
        *        *
```

Of the foregoing peptides, env1, env2, env3 and gag1 are particularly contemplated for diagnostic purposes, and env4, env5, env6, env7, env8, env9, env10 and env11 are particularly contemplated as protecting agents. These peptides have been selected in part because of their sequence homology to certain of the envelope and gag protein products of other of the retroviruses in the HIV group. For vaccinating purposes, the fore going peptides may be coupled to a carrier protein by utilizing suitable and well known techniques to enhance the host's immune response. Adjuvants such as calcium phosphate or alum hydroxide may also be added. The foregoing peptides can be synthesized by conventional protein synthesis techniques, such as that of Merrifield.

It will be apparent to those skilled in the art that various modifications and variations can be made in the processes and products of the present invention. Thus, it is intended that the present application cover the modifications and variations of this invention provided they come within the scope of the appended claims and their equivalents. For convenience in interpreting the following claims, the following table sets forth the correspondence between codon codes and amino acids and the correspondence between three-letter and one-letter amino acid symbols.

| | | DNA CODON | | | | AMINO ACID 3 LET. | | | | AMINO ACID 1 LET. | | | |
|---|---|---|---|---|---|---|---|---|---|---|---|---|---|
| 1 | \2 3\ | T | C | A | G | T | C | A | G | T | C | A | G |
| | T | TTT | TCT | TAT | TGT | PHE | SER | TYR | CYS | F | S | Y | C |
| T | C | TTC | TCC | TAC | TGC | PHE | SER | TYR | CYS | F | S | Y | C |
| | A | TTA | TCA | TAA | TGA | LEU | SER | *** | *** | L | S | * | * |
| | G | TTG | TCG | TAG | TGG | LEU | SER | *** | TRP | L | S | * | W |
| | T | CTT | CCT | CAT | CGT | LEU | PRO | HIS | ARG | L | P | H | R |
| C | C | CTC | CCC | CAC | CGC | LEU | PRO | HIS | ARG | L | P | H | R |
| | A | CTA | CCA | CAA | CGA | LEU | PRO | GLN | ARG | L | P | Q | R |
| | G | CTG | CCG | CAG | CGG | LEU | PRO | GLN | ARG | L | P | Q | R |
| | T | ATT | ACT | AAT | AGT | ILE | THR | ASN | SER | I | T | N | S |
| A | C | ATC | ACC | AAC | AGC | ILE | THR | ASN | SER | I | T | N | S |
| | A | ATA | ACA | AAA | AGA | ILE | THR | LYS | ARG | I | T | K | R |
| | G | ATG | ACG | AAG | AGG | MET | THR | LYS | ARG | M | T | K | R |
| | T | GTT | GCT | GAT | GGT | VAL | ALA | ASP | GLY | V | A | D | G |
| G | C | GTC | GCC | GAC | GGC | VAL | ALA | ASP | GLY | V | A | D | G |
| | A | GTA | GCA | GAA | GGA | VAL | ALA | GLU | GLY | V | A | E | G |
| | G | GTG | GCG | GAG | GGG | VAL | ALA | GLU | GLY | V | A | E | G |

| 3 Letter | 1 Letter | CODONS |
|---|---|---|
| ALA | A | GCT GCC GCA GCG |

-continued

| DNA CODON | AMINO ACID 3 LET. | AMINO ACID 1 LET. |
|---|---|---|
| ARG | R | CGT CGC CGA CGG AGA AGG |
| ASN | N | AAT AAC |
| ASP | D | GAT GAC |
| CYS | C | TGT TGC |
| GLN | Q | CAA CAG |
| GLU | E | GAA GAG |
| GLY | G | GGT GGC CGA GGG |
| HIS | H | CAT CAC |
| ILE | I | ATT ATC ATA |
| LEU | L | CTT CTC CTA CTG TTA TTG |
| LYS | K | AAA AAG |
| MET | M | ATG |
| PHE | F | TTT TTC |
| PRO | P | CCT CCC CCA CCG |
| SER | S | TCT TCC TCA TCG AGT AGC |
| THR | T | ACT ACC ACA ACG |
| TRP | W | TGG |
| TYR | Y | TAT TAC |
| VAL | V | GTT GTC GTA GTG |
| *** | * | TAA TAG TGA |

What is claimed is:

1. A nucleic acid of HIV-2 having the nucleotide sequence of a full length pol gene as set forth in FIG. 6.

* * * * *

UNITED STATES PATENT AND TRADEMARK OFFICE
CERTIFICATE OF CORRECTION

PATENT NO. : 6,355,789 B1
DATED : March 12, 2002
INVENTOR(S) : Alizon et al.

It is certified that error appears in the above-identified patent and that said Letters Patent is hereby corrected as shown below:

Delete the title page and substitute the attached title page.

Delete drawing sheets 1A-5 and substiute the attached drawing sheets 1-10 consisting of figs 1A-6E.

Signed and Sealed this

Seventh Day of February, 2006

JON W. DUDAS
*Director of the United States Patent and Trademark Office*

United States Patent
Alizon et al.

(10) Patent No.: US 6,355,789 B1
(45) Date of Patent: Mar. 12, 2002

(54) CLONED DNA SEQUENCES RELATED TO THE ENTIRE GENOMIC RNA OF HUMAN IMMUNODEFICIENCY VIRUS II (HIV-2), POLYPEPTIDES ENCODED BY THESE DNA SEQUENCES AND USE OF THESE DNA CLONES AND POLYPEPTIDES IN DIAGNOSTIC KITS

(75) Inventors: Marc Alizon, Paris; Luc Montagnier, Le Plessis Robinson; Denise Geutard, Paris, all of (FR); Francois Clavel, Rockville, MD (US); Pierre Sonigo; Mireille Guyader, both of Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 08/468,424

(22) Filed: Jun. 6, 1995

Related U.S. Application Data

(63) Continuation of application No. 08/214,221, filed on Mar. 17, 1994, now Pat. No. 5,580,739, which is a division of application No. 07/810,908, filed on Dec. 20, 1991, which is a division of application No. 07/752,368, filed on Sep. 3, 1991, now abandoned, which is a division of application No. 07/013,477, filed on Feb. 11, 1987, now Pat. No. 5,079,342, which is a continuation-in-part of application No. 07/003,764, filed on Jan. 16, 1987, now Pat. No. 5,051,496, which is a continuation-in-part of application No. 06/933,184, filed on Nov. 21, 1986, now abandoned, which is a continuation-in-part of application No. 06/916,080, filed on Oct. 6, 1986, now abandoned, which is a continuation-in-part of application No. 06/835,228, filed on Mar. 3, 1986, now Pat. No. 4,839,288.

(30) Foreign Application Priority Data

| Jan. 22, 1986 | (FR) | 86 00911 |
| Feb. 6, 1986 | (FR) | 86 01635 |
| Feb. 13, 1986 | (FR) | 86 01985 |
| Mar. 18, 1986 | (FR) | 86 03863 |
| Mar. 24, 1986 | (FR) | 86 04215 |

(51) Int. Cl.$^7$ .................................... C07H 21/04
(52) U.S. Cl. ............... 536/23.72; 536/23.1; 424/188.1; 424/208.1
(58) Field of Search .................. 435/91.32, 91.51, 435/172.3; 424/208.1; 536/23.77

(56) References Cited

U.S. PATENT DOCUMENTS

| 4,629,783 A | 12/1986 | Co and .................. 424/188.1 |
| 4,839,288 A | 6/1989 | Montagnier et al. ........ 435/235 |
| 5,079,342 A | 1/1992 | Alizon et al. ............. 530/324 |
| 5,670,309 A | 9/1997 | Murphy et al. ............... 435/5 |

FOREIGN PATENT DOCUMENTS

| EP | 0 316 695 B1 | 3/1993 |
| WO | WO 85/04674 | 11/1985 |

OTHER PUBLICATIONS

Gao, F., et al., 1994, "Genetic diversity of human immunodeficiency virus type 2: Evidence for distinct sequence subtypes with differences in virus biology.", J. Virol. 68(11):7433–7447.*

Goodenow, M., et al., 1989, "HIV–1 isolates are rapidly evolving quasispecies: Evidence for viral mixtures and preferred nucleotide substitutions.", J. Acquir. Immun. Defic. Syndr. 2:344–352.*

Holland, J.J., et al., 1992, "RNA virus populations as quasispecies", Curr. Topics Microbiol. Immunol. 176:1–20.*

Los Alamos Database, 1990, in Human Retroviruses and AIDS, Myers et al., eds., Los Alamos National Laboratory, New Mexico, pp. IA1–IA3.*

Tedder et al., 1988, The Lancet 2:927–931.*

Hunt et al., 1990, AIDS Res. Human Retro. 6:883–898.*

Strongin, W., 1992, "Sensitivity, specificity, and predictive value of diagnostic tests: definitions and clinical applications", in Laboratory Diagnosis of Viral Infections, Lennette ed., Marcel Dekker, Inc. New York, pp. 211–219.*

Clavel et al., "Isolation of a New Human Retrovirus from West African Patients with AIDS", *Science*, 233, pp. 343–346 (1986).

Allan et al., "Major Glycoprotein Antigens That Induce Antibodies in AIDS Patients Are Encoded by HTLV–III," *Science*, 228, pp. 1091–1094 (1985).

(List continued on next page.)

*Primary Examiner*—Laurie Scheiner
*Assistant Examiner*—Jeffrey S. Parkin
(74) *Attorney, Agent, or Firm*—Finnegan, Henderson, Farabow, Garrett, & Dunner, LLP

(57) ABSTRACT

The present invention is directed toward nucleic acids containing the full-length human immunodeficiency virus type 2 ROD (HIV-$2_{ROD}$) pol gene. HIV-2, which was originally designated lymphadenopathy-associated virus type II (LAV-II), was isolated from AIDS patients in West Africa. The virus is genotypically and phenotypically distinct from HIV-1 and bears a closer genetic relationship to the simian immunodeficiency virus (SIV). The present invention describes the preparation of HIV-$2_{ROD}$ proviral molecular clones from a genomic lambda phage library of CD4$^+$-infected cells. The complete nucleotide sequence of the full-length genome was determined and the putative gag, pol, env, vif (Q), vpr (R), vpx (X), nef (F), tat, and rev (art) genes identified. The claimed invention is directed toward nucleic acids containing the full-length HIV-$2_{ROD}$ pol gene (nt 1829–4936). These nucleic acids should prove useful as diagnostic reagents for the detection of HIV-2 and facilitate expression of the pol gene product.

1 Claim, 10 Drawing Sheets

FIG. IA

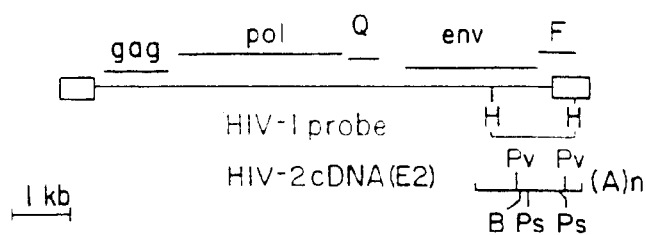

FIG. IB

```
                              PvuI         PstI
HIV.2   AGTAACTAACAGAA------ACAGCTGAGACTGC----AGGGACTTTCCAGAAGGGGCTG
HIV.1   AGT-ACTTCAAGAACTGCTGACATC-GAGCTTGCTACAAGGGACTTTCCGCTGGGGACTT
             9000       9010       9020       9030       9040

HIV.2   TAACCAA-------------GGGAGGGACATGGGAG----GAGCTGGTGGGGAACGCCTC
HIV.1   T--CCAGGGAGGCGTGGCCTGGGCGGGACTGGGGAGTGGCGAGC------------CCTC
           9050       9060       9070       9080       9090

HIV.2   ATATTCTCTGTATAAATATACCCGCTGCTTGCATTGTACTTCAGTCGCTCTGCGGAGAGG
HIV.1   AGATG--CTGCATATAAGCAGCTGCTTTTTGCC-TGTACTGG-GTCTCTCTGGTTAGAC-
            9100       9110       9120       9130       9140
                                                  U3  R

HIV.2   CTGGCAGATTGAGCCCTGGGAGGTTCTCTCCAGCACTAGCAGGTAGAGCCTGGGTGTCCC
HIV.1   ----CAGATTTGAGCCTGGGAGC-TCTCTGGCTAACTAGGGAACCCAC-----------
            9150       9160       9170       9180       9190

HIV.2   TGCTAGACTCTCACCAGCACTTGGCCGGTGCTGGGCAGACGGCCCCACGCTTGCTTGCTT
HIV.1   ------------------------------------------------------TGCTT

HIV.2   AAAAACCTCCTTAATAAAGCT-GCC---AGTAGAAGCA
HIV.1   AAG-----CCTCAATAAAGCTTGCCTTGAGTGCTTCAA
                    9210      9220                R
                    HindIII
```

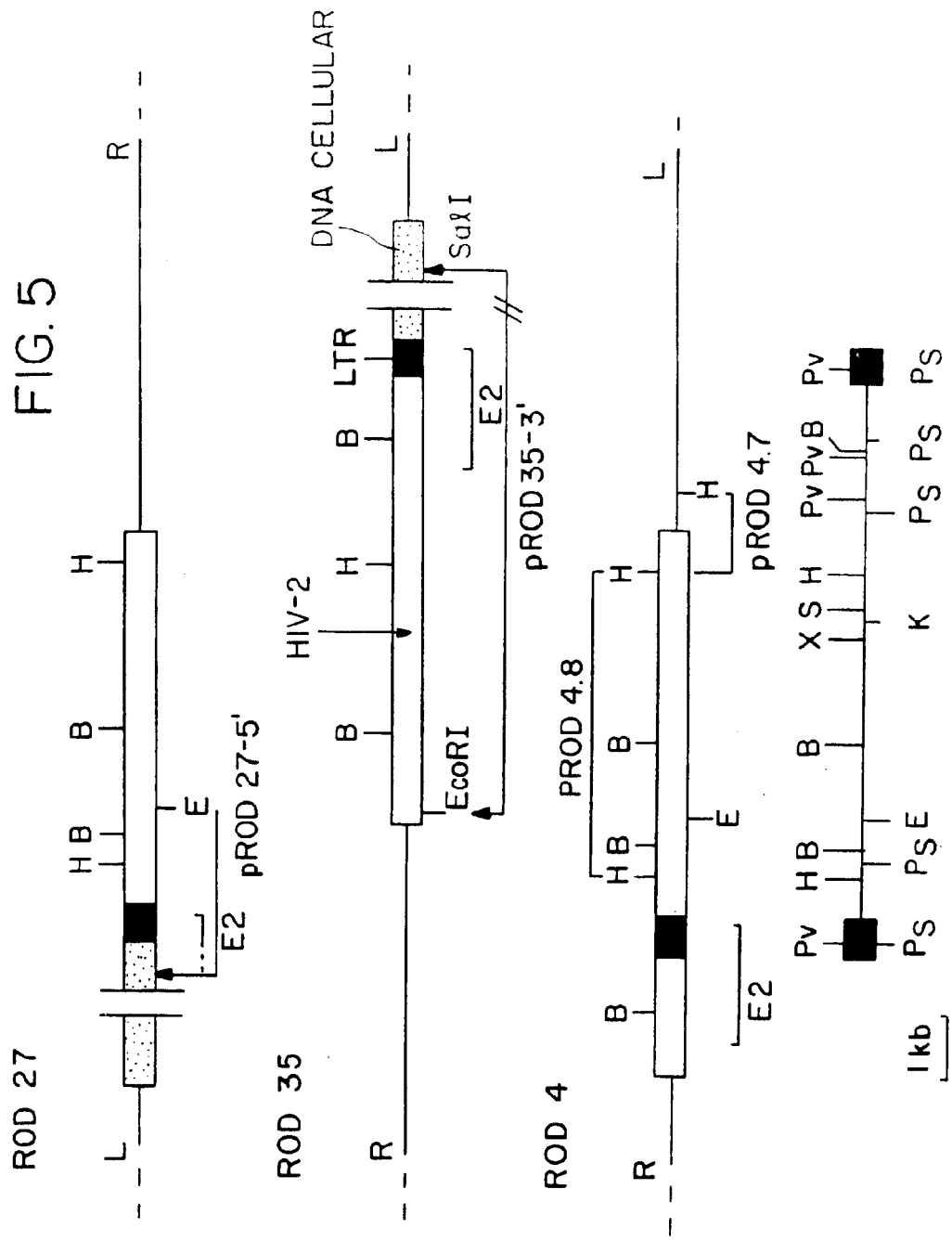

```
                        ThrGlyArgPhePheArgThrGlyProLeuGly
                        GlnAlaGlyPheLeuGlyLeuGlyProTrpGly
                        ACAGGCAGGTTTTTTAGGACTGGGCCCTTGGG
                            *           *           *           *
    LysGluAlaProGlnLeuProArgGlyProSerSerAlaGlyAlaAspThrAsnSerThr
    LysLysProArgAsnPheProValAlaGlnValProGlnGlyLeuThrProThrAlaPro
    GAAAGAAGCCCCGCAACTTCCCCGTGGCCCAAGTTCCGCAGGGGCTGACACCAACAGCAC
         *           *           *          1900         *           *
    ProSerGlySerSerSerGlySerThrGlyGluIleTyrAlaAlaArgGluLysThrGlu
    ProValAspProAlaValAspLeuLeuGluLysTyrMetGlnGlnGlyLysArgGlnArg
    CCCCAGTGGATCCAGCAGTGGATCTACTGGAGAAATATATGCAGCAAGGGAAAAGACAGA
         *           *           *           *           *           *
    ArgAlaGluArgGluThrIleGlnGlySerAspArgGlyLeuThrAlaProArgAlaGly
    GluGlnArgGluArgProTyrLysGluValThrGluAspLeuLeuHisLeuGluGlnGly
    GAGAGCAGAGAGAGAGACCATACAAGGAAGTGACAGAGGCTTACTGCACCTGCGAGCAGG
         *          2000         *           *           *           *
    GlyAspThrIleGlnGlyAlaThrAsnArgGlyLeuAlaAlaProGlnPheSerLeuTrp
    GluThrProTyrArgGluProProThrGluAspLeuLeuHisLeuAsnSerLeuPheGly
    GGGAGACACCATACAGGGAGCCAACCACAGAGGACTTGCTGCACCTCAATTCTCTCTTTG
         *           *           *           *           *          2100
    LysArgProValValThrAlaTyrIleGluGlyGlnProValGluValLeuLeuAspThr
    LysAspGln
    GAAAAGACCAGTAGTCACAGCATACATTGAGGGTCAGCCAGTAGAAGTCTTGTTAGACAC
         *           *           *           *           *           *
    GlyAlaAspAspSerIleValAlaGlyIleGluLeuGlyAsnAsnTyrSerProLysIle
    AGGGGCTGACGACTCAATAGTAGCAGGAATAGAGTTAGGGAACAATTATAGCCCAAAAAT
         *           *           *          2200         *           *
    ValGlyGlyIleGlyGlyPheIleAsnThrLysGluTyrLysAsnValGluIleGluVal
    AGTAGGGGGAATAGGGGGATTCATAAATACCAAGGAATATAAAAATGTAGAAATAGAAGT
         *           *           *           *           *           *
    LeuAsnLysLysValArgAlaThrIleMetThrGlyAspThrProIleAsnIlePheGly
    TCTAAATAAAAAGGTACGGGCTACCATAATGACAGGCGATACCCCAATCAACATTTTTGG
         *           *           *           *           *           *
    ArgAsnIleLeuThrAlaLeuGlyMetSerLeuAsnLeuProValAlaLysValGluPro
    CAGAAATATTCTGACAGCCTTAGGCATGTCATTAAATCTACCAGTCGCCAAAGTAGAGCC
         *           *           *           *           *          2400
    AATAAAAATAATGCTAAAGCCAGGGAAGATGGACCAAAACTGAGACAATGGCCCTTAAC
         *           *           *           *           *           *
```

FIG. 6A

```
LysGluLysIleGluAlaLeuLysGluIleCysGluLysMetGluLysGluGlyGlnLeu
AAAAGAAAAAATAGAAGCACTAAAAGAAATCTGTGAAAAAATGGAAAAAGAAGGCCAGCT
         *         *         *        2500       *         *
GluGluAlaProProThrAsnProTyrAsnThrProThrPheAlaIleLysLysLysAsp
AGAGGAAGCACCTCCAACTAATCCTTATAATACCCCCACATTTGCAATCAAGAAAAAGGA
         *         *         *         *         *         *
LysAsnLysTrpArgMetLeuIleAspPheArgGluLeuAsnLysValThrGlnAspPhe
CAAAAACAAATGGAGGATGCTAATAGATTTCAGAGAACTAAACAAGGTAACTCAAGATTT
         *       2600       *         *         *         *
ThrGluIleGlnLeuGlyIleProHisProAlaGlyLeuAlaLysLysArgArgIleThr
CACAGAAATTCAGTTAGGAATTCCACACCCAGCAGGGTTGGCCAAGAAGAGAAGAATTAC
         *         *         *         *         *       2700
ValLeuAspValGlyAspAlaTyrPheSerIleProLeuHisGluAspPheArgProTyr
TGTACTAGATGTAGGGGATGCTTACTTTTCCATACCACTACATGAGGACTTTAGACCATA
         *         *         *         *         *         *
ThrAlaPheThrLeuProSerValAsnAsnAlaGluProGlyLysArgTyrIleTyrLys
TACTGCATTTACTCTACCATCAGTGAACAATGCAGAACCAGGAAAAAGATACATATATAA
         *         *         *       2800        *         *
ValLeuProGlnGlyTrpLysGlySerProAlaIlePheGlnHisThrMetArgGlnVal
AGTCTTGCCACAGGGATGGAAGGGATCACCAGCAATTTTTCAACACACAATGAGACAGGT
         *         *         *         *         *         *
LeuGluProPheArgLysAlaAsnLysAspValIleIleIleGlnTyrMetAspAspIle
ATTAGAACCATTCAGAAAAGCAAACAAGGATGTCATTATCATTCAGTACATGGATGATAT
         *       2900       *         *         *         *
LeuIleAlaSerAspArgThrAspLeuGluHisAspArgValValLeuGlnLeuLysGlu
CTTAATAGCTAGTGACAGGACAGATTTAGAACATGATAGGGTAGTCCTGCAGCTCAAGGA
         *         *         *         *         *       3000
LeuLeuAsnGlyLeuGlyPheSerThrProAspGluLysPheGlnLysAspProProTyr
ACTTCTAAATGGCCTAGGATTTTCTACCCCAGATGAGAAGTTCCAAAAAGACCCTCCATA
         *         *         *         *         *         *
HisTrpMetGlyTyrGluLeuTrpProThrLysTrpLysLeuGlnLysIleGlnLeuPro
CCACTGGATGGGCTATGAACTATGGCCAACTAAATGGAAGTTGCAGAAAATACAGTTGCC
         *         *         *       3100        *         *
GlnLysGluIleTrpThrValAsnAspIleGlnLysLeuValGlyValLeuAsnTrpAla
CCAAAAGAAATATGGACAGTCAATGACATCCAGAAGCTAGTGGGTGTCCTAAATTGGGC
         *         *         *         *         *         *
AlaGlnLeuTyrProGlyIleLysThrLysHisLeuCysArgLeuIleArgGlyLysLys
AGCACAACTCTACCCAGGGATAAAGACCAAACACTTATGTAGGTTAATCAGAGGAAAAAT
         *       3200       *         *         *         *
```

FIG. 6B

```
ThrLeuThrGluGluValGlnTrpThrGluLeuAlaGluAlaGluLeuGluGluAsnArg
GACACTCACAGAAGAAGTACAGTGGACAGAATTACCAGAAGGAGAGCTAGAAGAAAACAG
        *         *         *         *         *        3300
  IleIleLeuSerGlnGluGlnGluGlyHisTyrTyrGlnGluGluLysGluLeuGluAla
AATTATCCTAAGCCAGGAACAAGAGGGACACTATTACCAAGAAGAAAAAGAGCTAGAAGC
        *         *         *         *         *         *
   ThrValGlnLysAspGlnGluAsnGlnTrpThrTyrLysIleHisGlnGluGluLysIle
AACAGTCCAAAAGGATCAAGAGAATCAGTGGACATATAAAATACACCAGGAAGAAAAAAT
        *         *         *        3400        *         *
   LeuLysValGluLysTyrAlaLysValLysAsnThrHisThrAsnGlyIleArgLeuLeu
TCTAAAAGTAGGAAAATATGCAAGGTGAAAAAACACCCATACCAATGGAATCAGATTGTT
        *         *         *         *         *         *
   AlaGlnValValGlnLysIleGlyLysGluAlaLeuValIleTrpGlyArgIleProLys
AGCACAGGTAGTTCAGAAAATAGGAAAAGAAGCACTAGTCATTTGGGGACGAATACCAAA
        *        3500        *         *         *         *
   PheHisLeuProValGluArgGluIleTrpGluGlnTrpTrpAspAsnTyrTrpGlnVal
ATTTCACCTACCAGTAGAGAGAGAAATCTGGGAGCAGTGGTGGGATAACTACTGGCAAGT
        *         *         *         *         *        3600
   ThrTrpIleProAspTrpAspPheValSerThrProProLeuValArgLeuAlaPheAsn
GACATGGATCCCAGACTGGGACTTCGTGTCTACCCCACCACTGGTCAGGTTAGCGTTTAA
        *         *         *         *         *         *
   LeuValGlyAspProIleProGlyAlaGluThrPheTyrThrAspGlySerCysAsnArg
CCTGGTAGGGGATCCTATACCAGGTGCAGAGACCTTCTACACAGATGGATCCTGCAATAG
        *         *         *        3700        *         *
   GlnSerLysGluGlyLysAlaGlyTyrValThrAspArgGlyLysAspLysValLysLys
GCAATCAAAAGAAGGAAAAGCAGGATATGTAACAGATAGAGGGAAAGACAAGGTAAAGAA
        *         *         *         *         *         *
   LeuGluGlnThrThrAsnGlnGlnAlaGluLeuGluAlaPheAlaMetAlaLeuThrAsp
ACTAGAGCAAACTACCAATCAGCAAGCAGAACTAGAAGCCTTTGCGATGGCACTAACAGA
        *        3800        *         *         *         *
   SerGlyProLysValAsnIleIleValAspSerGlnTyrValMetGlyIleSerAlaSer
CTCGGGTCCAAAAGTTAATATTATAGTAGACTCACAGTATGTAATGGGGATCAGTGCAAG
        *         *         *         *         *        3900
   GlnProThrGluSerGluSerLysIleValAsnGlnIleIleGluGluMetIleLysLys
CCAACCAACAGAGTCAGAAAGTAAAATAGTGAACCAGATCATAGAAGAAATGATAAAAAA
        *         *         *         *         *         *
   GluAlaIleTyrValAlaTrpValProAlaHisLysGlyIleGlyGlyAsnGlnGluVal
GGAAGCAATCTATGTTGCATGGGTCCCAGCCCACAAAGGCATAGGGGGAAACCAGGAAGT
        *         *         *        4000        *         *
```

*FIG. 6C*

```
AspHisLeuValSerGlnGlyIleArgGlnValLeuPheLeuGluLysIleGluProAla
AGATCATTTAGTGAGTCAGGGTATCAGACAAGTGTTGTTCCTGGAAAAAATAGAGCCCGC
       *         *         *         *         *         *
GlnGluGluHisGluLysTyrHisSerAsnValLysGluLeuSerHisLysPheGlyIle
TCAGGAAGAACATGAAAAATATCATAGCAATGTAAAAGAACTGTCTCATAAATTTGGAAT
       *       4100       *.        *         *         *
ProAsnLeuValAlaArgGlnIleValAsnSerCysAlaGlnCysGlnGlnLysGlyGlu
ACCCAATTTAGTGGCAAGGCAAATAGTAAACTCATGTGCCCAATGTCAACAGAAAGGGGA
       *         *         *         *         *       4200
AlaIleHisGlyGlnValAsnAlaGluLeuGlyThrTrpGlnMetAspCysThrHisLeu
AGCTATACATGGGCAAGTAAATGCAGAACTAGGCACTTGGCAAATGGACTGCACACATTT
       *         *         *         *         *         *
GluGlyLysIleIleIleValAlaValHisValAlaSerGlyPheIleGluAlaGluVal
AGAAGGAAAGATCATTATAGTAGCAGTACATGTTGCAAGTGGATTTATAGAAGCAGAAGT
       *         *         *       4300        *         *
IleProGlnGluSerGlyArgGlnThrAlaLeuPheLeuLeuLysLeuAlaSerArgTrp
CATCCCACAGGAATCAGGAAGACAAAGAGCACTCTTCCTATTGAAACTGGCAAGTAGGTG
       *         *         *         *         *         *
ProIleThrHisLeuHisThrAspAsnGlyAlaAsnPheThrSerGlnGluValLysMet
GCCAATAACACACTTGCATACAGATAATGGTGCCAACTTCACTTCACAGGAGGTGAAGAT
       *       4400        *         *         *         *
ValAlaTrpTrpIleGlyIleGluGlnSerPheGlyValProTyrAsnProGlnSerGln
GGTAGCATGGTGGATAGGTATAGAACAATCCTTTGGAGTACCTTACAATCCACAGAGCCA
       *         *         *         *         *       4500
GlyValValGluAlaMetAsnHisHisLeuLysAsnGlnIleSerArgIleArgGluGln
AGGAGTAGTAAGCAATGAATCACCATCTAAAAAAAACCAAATAAGTAGAATCAGAGAACA
       *         *         *         *         *         *
AlaAsnThrIleGluThrIleValLeuMetAlaIleHisCysMetAsnPheLysArgArg
GGCAAATACAATAGAAACAATAGTACTAATGGCAATTCATTGCATGAATTTTAAAAGAAG
       *         *         *       4600        *         *
GlyGlyIleGlyAspMetThrProSerGluArgLeuIleAsnMetIleThrThrGluGln
GGGGGGAATAGGGATATGACTCCATCAGAAAGATTAATCAATATGATCACCACAGAAACA
       *         *         *         *         *         *
GluIleGlnPheLeuGlnAlaLysAsnSerLysLeuLysAspPheArgValTyrPheArg
AGAGATACAATTCCTCCAAGCCAAAAATTCAAAATTAAAAGATTTTCGGGTATTTAACAG
       *       4700        *         *         *         *
GluGlyArgAspGlnLeuTrpLysGlyProGlyGluLeuLeuTrpLysGlyGluGlyAla
AGAAGGCAGAGATCAGTTGTGGAAAGGACCTGGGGAACTACTGTGGAAAGGAGAAGGAGC
       *         *         *         *         *       4800
```

FIG. 6D

```
ValLeuValLysGlyThrAspIleLysIleIleIleProArgArgLysAlaLysIleIle
AGTCCTAGTCAAGGTAGGAACAGACATAAAAATAATACCAAGAAGGAAAGCCAAGATCAT
         *         *         *         *         *         *
  ArgAspTyrGlyGlyArgGlnGluMetAspSerGlySerHisLeuGluGlyAlaArgGlu
          MetGluAspLysArgTrpIleValValProThrTrpArgValProGlyArg
CAGACACTATGGAGGAAGACAAGAGATGGATAGTGGTTCCCACCTGGAGGGTGCCAGGGA
         *         *         *        4900        *         *
AspGlyGluMetAla
  MetGluLysTrpHis
GGATGGAGAAATGGCA
         *         *
```

FIG. 6E